United States Patent [19]

Sakashita et al.

[11] Patent Number: 5,457,084

[45] Date of Patent: Oct. 10, 1995

[54] SUBSTITUTED PYRIDINESULFONAMIDE COMPOUND OR ITS SALT, PROCESS FOR PREPARING THE SAME, AND HERBICIDE CONTAINING THE SAME

[75] Inventors: Nobuyuki Sakashita, Shiga, Japan; Toshio Nakajima, Sunnyvale, Calif.; Shigeo Murai, Shiga, Japan; Kazuyuki Maeda, Shiga, Japan; Yuji Nakamura, Shiga, Japan; Tsunezo Yoshida, Shiga, Japan; Shooichi Honzawa, Shiga, Japan; Fumio Kanamori, Shiga, Japan

[73] Assignee: Ishihara Sangyo Kaisha Ltd., Osaka, Japan

[21] Appl. No.: 240,896

[22] Filed: May 11, 1994

Related U.S. Application Data

[60] Division of Ser. No. 28,165, Mar. 9, 1993, Pat. No. 5,348,933, which is a continuation-in-part of Ser. No. 821,582, Jan. 15, 1992, abandoned.

[30] Foreign Application Priority Data

| Jan. 24, 1991 | [JP] | Japan | 3-85718 |
| Jul. 12, 1991 | [JP] | Japan | 3-265553 |
| Mar. 10, 1992 | [JP] | Japan | 4-101549 |
| Jul. 24, 1992 | [JP] | Japan | 4-239931 |

[51] Int. Cl.⁶ .................... C07D 239/42; A01N 43/54
[52] U.S. Cl. .................... 504/215; 544/331; 544/320; 544/321
[58] Field of Search .................... 544/320, 321, 544/331; 504/215

[56] References Cited

U.S. PATENT DOCUMENTS

| 4,946,494 | 8/1990 | Taylor | 544/209 |
| 5,032,166 | 7/1991 | Taylor | 544/209 |
| 5,139,565 | 8/1992 | Kimura et al. | 544/320 |
| 5,221,315 | 6/1993 | Fory | 544/331 |

FOREIGN PATENT DOCUMENTS

| 0314505 | 5/1989 | European Pat. Off. . |
| 451468 | 10/1991 | European Pat. Off. . |
| 496608 | 7/1992 | European Pat. Off. . |
| 0116518 | 1/1984 | Germany . |
| 4000503 | 7/1991 | Germany . |
| 9002308 | 7/1991 | WIPO . |

OTHER PUBLICATIONS

Patent Abstracts of Japan, vol. 017, No. 042, Jan. 26, 1993, JPA–42 57 580.
Patent Abstracts of Japan, vol. 017, No. 037, Jan. 25, 1993, JPA–42 53 974.

*Primary Examiner*—John M. Ford
*Attorney, Agent, or Firm*—Sughrue, Mion, Zinn, Macpeak & Seas

[57] ABSTRACT

A substituted pyridinesulfonamide compound or its salt represented by the following formula (I):

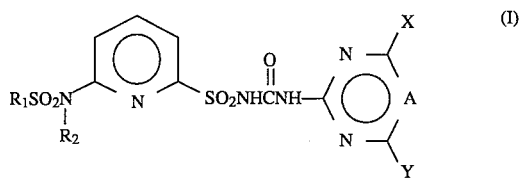

wherein A is CH; $R_1$ and $R_2$ are each independently a member selected from the group consisting of unsubstituted or substituted alkyl groups, unsubstituted or substituted alkenyl groups, unsubstituted or substituted cycloalkyl groups, and unsubstituted or substituted phenyl groups; and X and Y are each independently a member selected from the group consisting of alkyl groups and alkoxy groups. This compound is an effective ingredient in a herbicide showing a wide weed-control spectrum even when used in a small amount.

13 Claims, No Drawings

SUBSTITUTED PYRIDINESULFONAMIDE COMPOUND OR ITS SALT, PROCESS FOR PREPARING THE SAME, AND HERBICIDE CONTAINING THE SAME

This is a divisional of application Ser. No. 08/028,165 filed Mar. 9, 1993, now U.S. Pat. No. 5,348,933, which is a Continuation-in-Part of 07/821,582 filed Jan. 15, 1992, now abandoned.

FIELD OF THE INVENTION

The present invention relates to a novel substituted pyridinesulfonamide compound or its salt, a process for preparing the same, and a herbicide containing the same.

BACKGROUND OF THE INVENTION

U.S. Pat. No. 4,946,494 discloses a pyridinesulfonylurea derivative useful as an effective ingredient of a herbicidal composition, which is, however, different in the substituent at the 6-position of the pyridine ring in terms of chemical structure from the compound of the present invention.

EP 451,468 corresponding to U.S. Pat. No. 5,139,565 and PCT WO91/10660 disclose a pyridinesulfonylurea derivative as an active ingredient of herbicidal compositions. This compound is different from the compound of the present invention in the position of an N-substituted sulfamoyl group.

SUMMARY OF THE INVENTION

In accordance with one aspect of the present invention, there is provided a substituted pyridinesulfonamide compound or its salt represented by the following general formula (I):

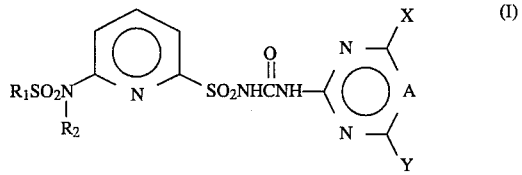

wherein A is CH or N; when A is CH, $R_1$ and $R_2$ may be either each independently a member selected from the group consisting of unsubstituted or substituted alkyl groups, unsubstituted or substituted alkenyl groups, unsubstituted or substituted cycloalkyl groups, and unsubstituted or substituted phenyl groups; when A is N, $R_1$ is an unsubstituted or substituted alkyl group, $R_2$ is an unsubstituted or substituted alkyl group, or an unsubstituted or substituted alkoxy group; and X and Y are each independently a member selected from the group consisting of alkyl groups and alkoxy groups.

In accordance with another aspect of the present invention, there is provided a process for preparing a substituted pyridinesulfonamide compound or its salt represented by the following general formula (I):

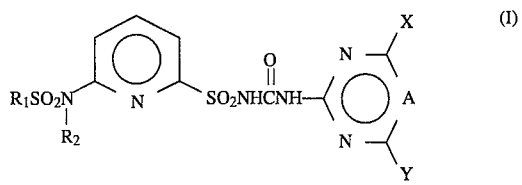

wherein A is CH or N; when A is CH, $R_1$ and $R_2$ may be either each independently a member selected from the group consisting of unsubstituted or substituted alkyl groups, unsubstituted or substituted alkenyl groups, unsubstituted or substituted cycloalkyl groups, and unsubstituted or substituted phenyl groups; when A is N, $R_1$ is an unsubstituted or substituted alkyl group, $R_2$ is an unsubstituted or substituted alkyl group, or an unsubstituted or substituted alkoxy group; and X and Y are each independently a member selected from the group consisting of alkyl groups and alkoxy groups, which comprises reacting a substituted pyridine compound represented by the following general formula (II):

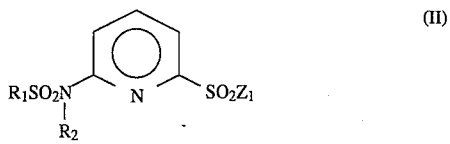

wherein $R_1$ and $R_2$ are the same as defined above; and $Z_1$ is a member selected from the group consisting of an —$NH_2$ group, an —NCO group, and —$NHCO_2R_3$ groups wherein $R_3$ is an alkyl or aryl group; with a pyrimidine or triazine compound represented by the following general formula (III):

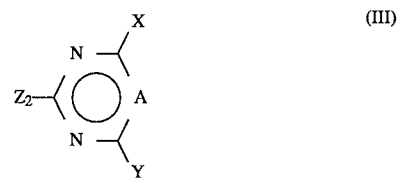

wherein A, X and Y are the same as defined above; and $Z_2$ is an —$NH_2$ group when $Z_1$ is an —NCO group or an —$NHCO_2R_3$ group, and is a member selected from the group consisting of an —NCO group and —$NHCO_2R_3$ groups wherein $R_3$ is the same as defined above, when $Z_1$ is an —$NH_2$ group.

In accordance with still another aspect of the present invention, there is provided a herbicide containing as the effective ingredient a substituted pyridinesulfonamide compound or its salt represented by the following general formula (I):

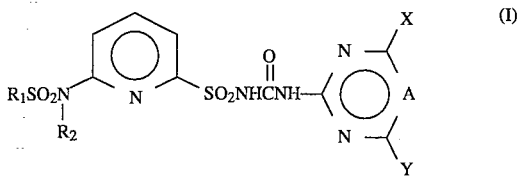

wherein A is CH or N; when A is CH, $R_1$ and $R_2$ may be either each independently a member selected from the group consisting of unsubstituted or substituted alkyl groups, unsubstituted or substituted alkenyl groups, unsubstituted or substituted cycloalkyl groups, and unsubstituted or substituted phenyl groups; when A is N, $R_1$ is an unsubstituted or substituted alkyl group, $R_2$ is an unsubstituted or substituted alkyl group, or an unsubstituted or substituted alkoxy group; and X and Y are each independently a member selected from the group consisting of alkyl groups and alkoxy groups.

In accordance with a further aspect of the present invention, there is provided a substituted pyridine compound represented by the following general formula (II-1') and (II-1"):

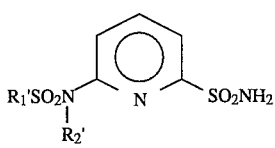

wherein $R_1'$ and $R_2'$ may be either each independently a member selected from the group consisting of unsubstituted or substituted alkyl groups, unsubstituted or substituted alkenyl groups, unsubstituted or substituted cycloalkyl groups, and unsubstituted or substituted phenyl groups.

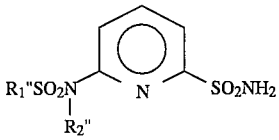

wherein $R_1''$ is an unsubstituted or substituted alkyl group, and $R_2''$ is an unsubstituted or substituted alkoxy group.

In accordance with a still further aspect of the present invention, there is provided a compound represented by the following general formula (IV') and (IV''):

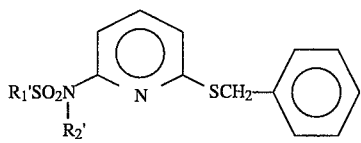

wherein $R_1'$ and $R_2'$ may be either each independently a member selected from the group consisting of unsubstituted or substituted alkyl groups, unsubstituted or substituted alkenyl groups, unsubstituted or substituted cycloalkyl groups, and unsubstituted or substituted phenyl groups.

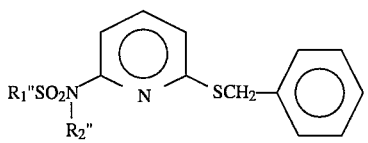

wherein $R_1''$ is an unsubstituted or substituted alkyl group, and $R_2''$ is an unsubstituted or substituted alkoxy group.

DETAILED DESCRIPTION OF THE INVENTION

The present invention will now be described in detail.

In the denotations of $R_1$ and $R_2$ in the general formula (I), the substituents that can be contained in the substituted alkyl groups, the substituted alkenyl groups and the substituted alkoxy group include halogen atoms, alkoxy groups, etc.; the substituents that can be contained in the substituted cycloalkyl groups include halogen atoms, alkyl groups, alkoxy groups, etc.; and the substituents that can be contained in the substituted phenyl groups include halogen atoms, alkyl groups, haloalkyl groups, a nitro group, etc. The number of substituent(s) contained in such a substituted group may be either one, or two or more, in which case the substituents may be the same or different from each other. The same applies to a substituent(s) if further contained in such a substituent as mentioned above that can be contained in such a substituted group that can be denoted by $R_1$ and $R_2$.

In the general formula (I), when A is CH, alkyl groups as well as alkyl moieties that may be included in the denotations of $R_1$, $R_2$, X and Y include those having 1 to 6 carbon atoms, such as methyl, ethyl, propyl, butyl, pentyl and hexyl groups that may each be linear or branched in terms of structural isomerism of the aliphatic chain. Alkenyl groups that may be included in the denotations of $R_1$ and $R_2$ include those having 2 to 6 carbon atoms, such as vinyl, propenyl, butenyl, pentenyl and hexenyl groups that may each be linear or branched in terms of structural isomerism of the aliphatic chain. Cycloalkyl groups that may be included in the denotations of $R_1$ and $R_2$ include those having 3 to 6 carbon atoms, such as cyclopropyl, cyclobutyl, cyclopentyl, and cyclohexyl groups. Halogen atoms that may be included in the denotations of $R_1$ and $R_2$ include fluorine, chlorine, bromine and iodine atoms.

In the general formula (I), when A is N, alkyl groups as well as alkyl moieties that may be included in the denotations of $R_1$, $R_2$, X and Y include those having 1 to 4 carbon atoms, such as methyl, ethyl, propyl and butyl groups that may each be linear or branched in terms of structural isomerism of the aliphatic chain. Halogen atoms that may be included in the denotations of $R_1$ and $R_2$ include fluorine, chlorine, bromine and iodine atoms.

Examples of the salt of the substituted pyridinesulfonamide compound represented by the general formula (I) include those of alkali metals such as sodium and potassium, those of alkaline earth metals such as magnesium and calcium, and those of amines such as dimethylamine and triethylamine.

The substituted pyridinesulfonamide compounds represented by the general formula (I) or salts thereof may include their several optical isomers depending on the substituent(s) $R_1$ and/or $R_2$.

Among the compounds of the formula (I), when A is CH, preferred are those wherein $R_1$ and $R_2$ may be either each independently a member selected from the group consisting of unsubstituted or substituted alkyl groups and unsubstituted or substituted cycloalkyl groups and X and Y are each independently a member selected from the group consisting of alkyl groups and alkoxy groups; more preferred are those wherein $R_1$ and $R_2$ may be either each independently a member selected from the group consisting of alkyl groups, haloalkyl groups, and cycloalkyl groups, and X and Y are each independently a member selected from the group consisting of alkyl groups and alkoxy groups; and most preferred are 6-[(N-ethyl-N-methylsulfonyl)amino]-N-[[(4, 6-dimethoxypyrimidin-2-yl)amino]carbonyl]- 2-pyridinesulfonamide (Compound No. α-2 as described hereinafter), 6-[(N-ethyl-N-ethylsulfonyl)amino]-N-[[(4,6-dimethoxypyrimidin-2-yl)amino]-carbonyl]-2-pyridinesulfonamide (Compound No. α-18 as described hereinafter) and 6-[(N-ethyl-N-isopropylsulfonyl)amino]-N-[ [(4,6-dimethoxypyrimidin-2-yl)amino]-carbonyl]-2-pyridinesulfonamide (Compound No. α-22 as described hereinafter).

Among the compounds of the formula (I), when A is N, preferred-are those wherein X and Y are each independently a member selected from the group consisting of methyl group and methoxy group; more preferred are those wherein $R_1$ and $R_2$ may be either each independently alkyl groups which include those having 2 to 4 carbon atoms, and X and Y are each independently a member selected from the group consisting of methyl group and methoxy group; and most preferred are 6-[(N-ethyl-N-isopropyl-sulfonyl)amino]-N-[ [(4-methoxy- 6methyltriazin-2-yl)-amino]carbonyl]-2-pyridinesulfonamide (Compound No. β-1 as described hereinafter), 6-[(N-ethyl-N-isopropylsulfonyl)amino]-N-[[(4,6- dimethoxytriazin-2-yl)amino]-carbonyl]-2-pyridinesulfonamide (Compound No. β-2 as described hereinafter), 6-[[N-(1-chloroethylsulfonyl)-N-ethyl]amino]-N-[[( 4-methoxy-6-methyltriazin-2-yl)amino]-carbonyl]-2-pyridinesulfonamide (Compound No. β-54 as described hereinafter), 6-[[N-(1-chloroethylsulfonyl)-N-ethyl]amino]-N-[[( 4,6-dimethoxytriazin-2-yl)amino]carbonyl]-2-pyridinesulfonamide (Compound No. β-55 as described hereinafter) and 6-[(N-dichloromethylsulfonyl-N-ethyl)amino]-N-[[(4,6-dimethoxytriazine-2-yl)amino]-carbonyl]-2-pyridinesulfonamide (Compound No. β-57 as described hereinafter).

The substituted pyridinesulfonamide compound represented by the general formula (I) can be prepared, for example, according to the process of the present invention, embodiments of which may be represented by the following reaction formulae [A] to [D]:

Reaction Formula [A]

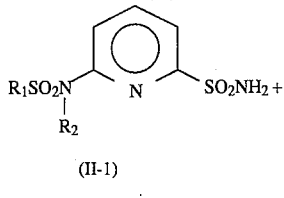

(II-1)

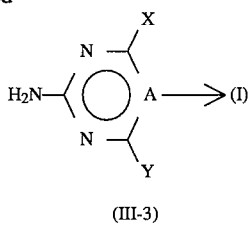

(III-1)

Reaction Formula [B]

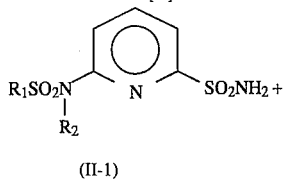

(II-1)

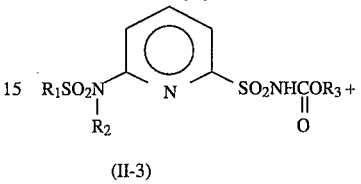

(III-2)

Reaction Formula [C]

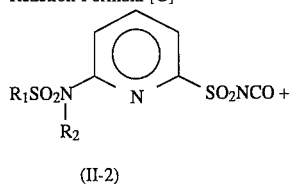

(II-2)

Reaction Formula [D]

$R_1SO_2N(R_2)$—⟨pyridine⟩—$SO_2NHCOR_3$ +

(II-3)

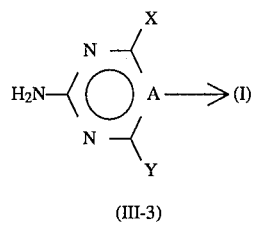

(III-3)

In the reaction formulae [A] to [D], A, $R_1$, $R_2$, X and Y are the same defined above, and $R_3$ is an alkyl group or an aryl group.

The alkyl group represented by $R_3$ includes alkyl groups having from 1 to 6 carbon atoms, which may be substituted with a halogen atom, an alkoxy group, etc. As the aryl group included in the denoration of $R_3$, there can be mentioned a phenyl group, a phenyl group substituted with at least one chlorine atom, a phenyl group substituted with at least one methyl group, a naphthyl group, etc.

The reaction [A] is effected in the presence of a base, while the reactions [B], [C] and [D] may be effected in the presence of a base if desired. Examples of such a base include tertiary amines such as triethylamine, and 1,8-diazabicyclo[5.4.0]-7-undecene.

The reactions [A], [B], [C] and [D] may be effected in the presence of a solvent if necessary. Examples of the solvent include unsubstituted or substituted, aromatic hydrocarbons such as benzene, toluene, xylene, and chlorobenzene; unsubstituted or substituted, cyclic or acyclic, aliphatic hydrocarbons such as chloroform, carbon tetrachloride, methylene chloride, dichloroethane, trichloroethane, hexane, and cyclohexane; ethers such as diethyl ether, dioxane, and tetrahydrofuran; nitriles such as acetonitrile, propionitrile, and acrylonitrile; esters such as methyl acetate and ethyl acetate; aprotic polar solvents such as dimethyl sulfoxide and sulfolane; etc.

The reaction temperature of the reaction [A] is usually in the range of −20° to +100° C., preferably in the range of 0° to 40° C., while the reaction time of the reaction [A] is usually in the range of 0.01 to 24 hours, preferably in the range of 0.1 to 1.5 hours. The reaction temperature of the reaction [B] is usually in the range of 0° to 150° C., while the reaction time of the reaction [B] is usually in the range of 0.1 to 24 hours. The reaction temperature of the reaction [C] is usually in the range of 0° to 150° C., while the reaction time of the reaction [C] is usually in the range of 0.1 to 24 hours. The reaction temperature of the reaction [D] is usually in the range of −20° to +150° C., while the reaction time of the reaction [D] is usually in the range of 0.1 to 24 hours.
A starting material compound represented by the general formula (II-1) in the reaction formulae [A] and [B] according to the present invention can be synthesized, for example, according to one of reaction formulae [E], [F] and [G]:
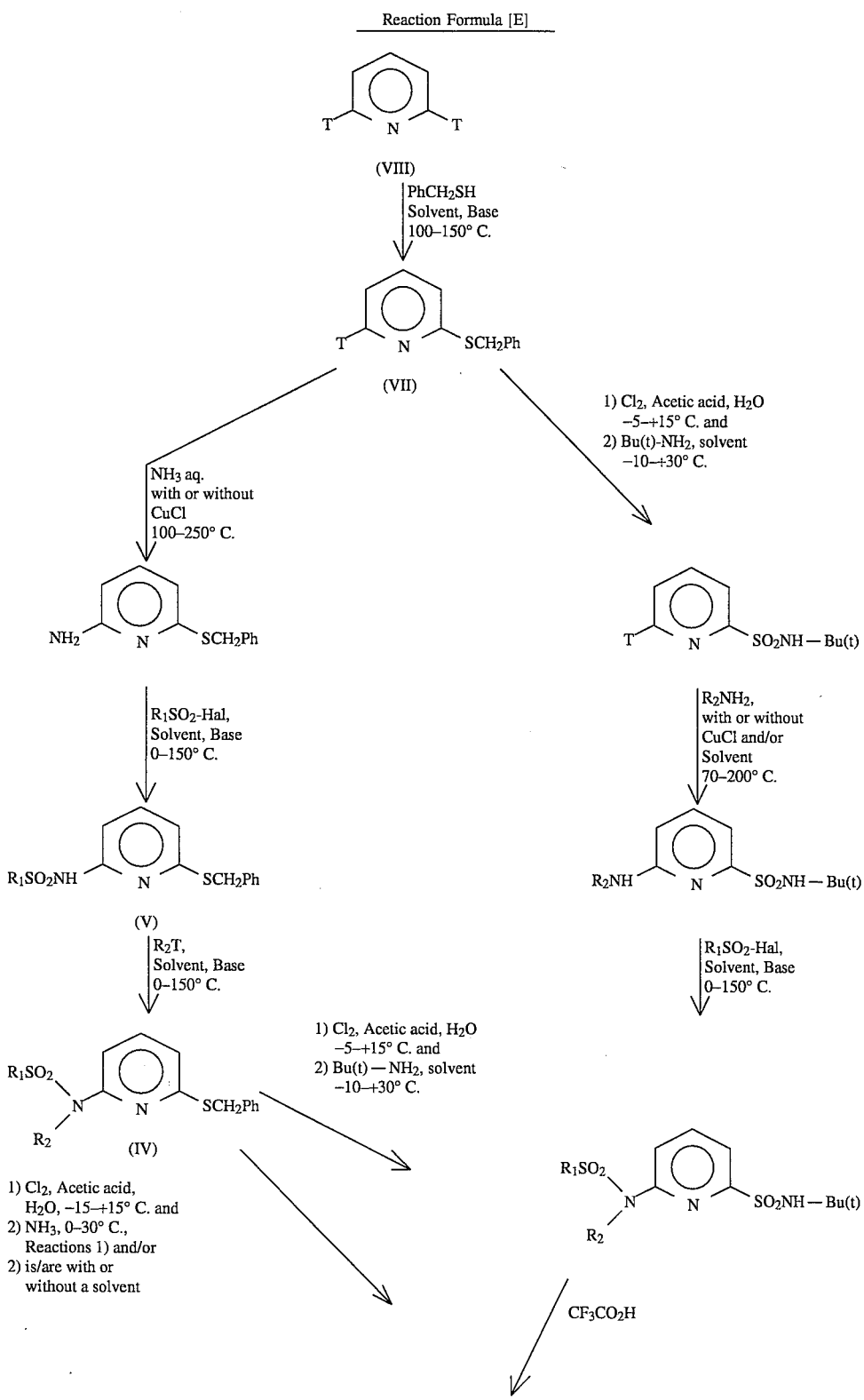

-continued
Reaction Formula [E]
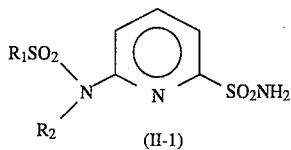
-continued
Reaction Formula [F]
(IV)
↓
(II-1)
Reaction Formula [F]
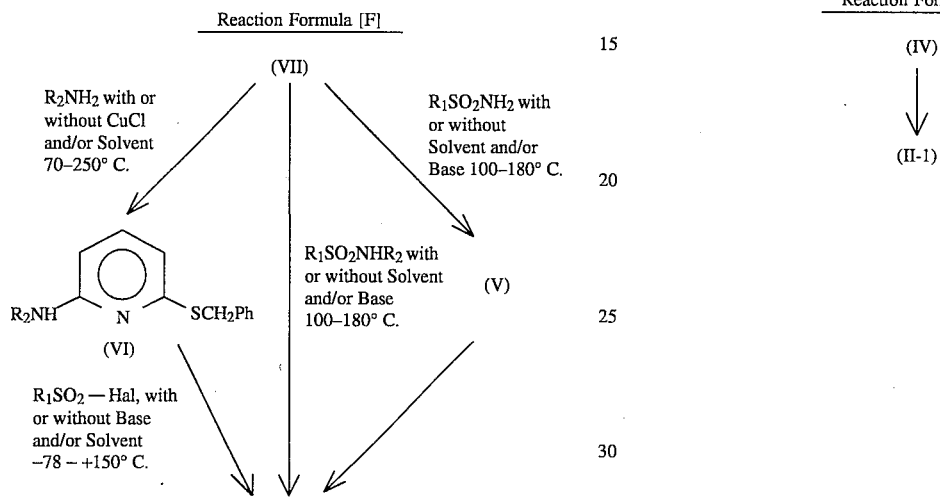
Reaction Formula [G]
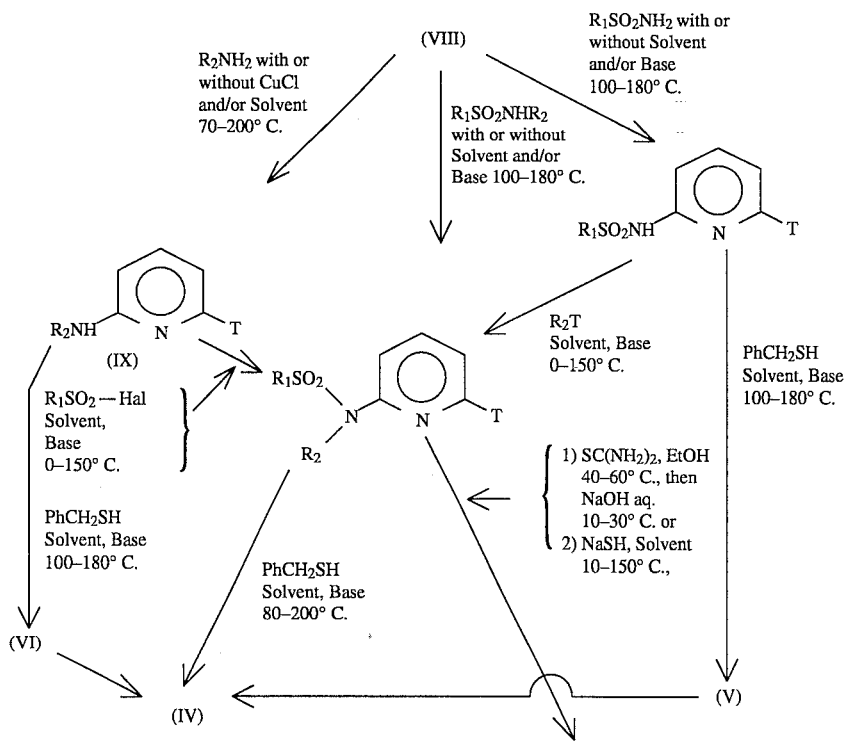

-continued

Reaction Formula [G]

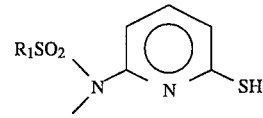

(II-1)

In the reaction formulae [E], [F] and [G], $R_1$ and $R_2$ are the same as defined above; Hal is a member selected from the group consisting of a fluorine atom, a chlorine atom, a bromine atom, and an iodine atom; T is a member selected from the group consisting of a chlorine atom, a bromine atom, and an iodine atom; Ph stands for a phenyl group; Et stands for an ethyl group; Bu(t) stands for a tertiary butyl group; and aq. stands for an aqueous solution.

The compound represented by the general formula (II-1) wherein $R_1$ is a halogen-substituted alkyl group may be prepared according to Reaction Formula H.

Reaction Formula H:

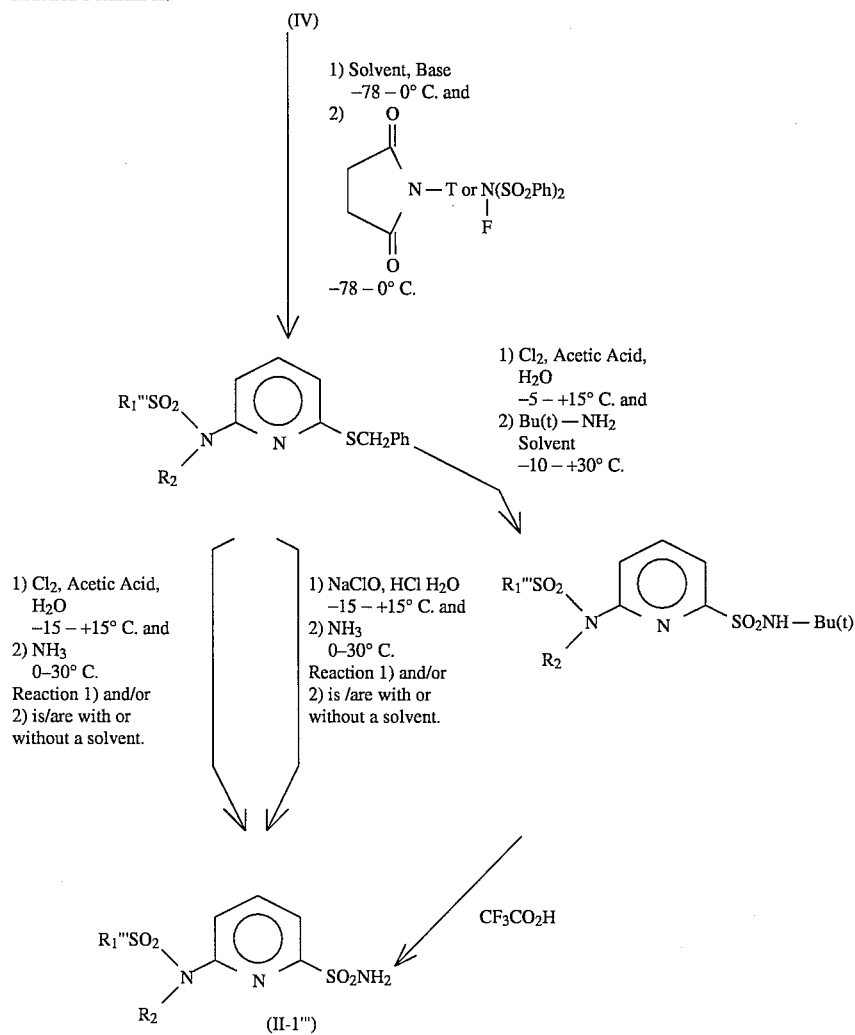

wherein $R_1'''$ represents a halogen-substituted alkyl group; and $R_2$, T, Ph, and Bu(t) are as defined above.

In Reaction Formula G, the compound represented by formula (IX) may be prepared according to Reaction Formula I:

Reaction Formula I:

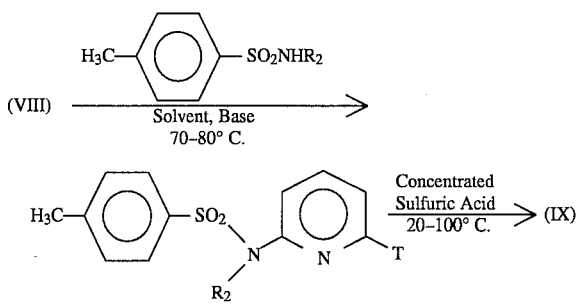

wherein $R_2$ and T are as defined above.

A starting material compound represented by the formula (II-2) in the reaction formula [C] can be prepared, for example, according to the following reaction formula [J]:

Reaction Formula [J]

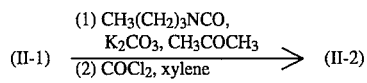

A starting material compound represented by the formula (II-3) in the reaction formula [D] can be prepared, for example, according to the following reaction formula [K]:

Reaction Formula [K]

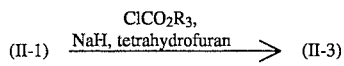

$R_1$, $R_2$ and $R_3$ in the reaction formulae [J] and [K] are the same as defined hereinbefore.

The reaction conditions of the reactions [E] to [K], which involve the reaction temperature, the period of reaction time, the use or disuse as well as kind and amount of solvent (to be used if desired), and the kind and amount of base, can usually be appropriately chosen from the reaction conditions of similar reactions unless otherwise mentioned.

The salt of the aforementioned substituted pyridinesulfonamide compound can be easily prepared according to a usual method.

The following Examples will specifically illustrate the present invention in more detail, but should not be construed as limiting the scope of the invention.

SYNTHESIS EXAMPLE 1

Synthesis of 6-[(N-ethyl-N-methylsulfonyl)amino]-N-[[(4, 6-dimethoxypyrimidin-2-yl)amino]carbonyl]- 2-pyridinesulfonamide (Compound No. α-2 in Table 2-α which will be given later)

1) 13 g of 2-benzylthio-6-bromopyridine, 80 ml of aqueous ammonia (about 40 wt %), and a catalytic amount of cuprous chloride were mixed together and reacted in an autoclave at 120° C. for 4 hours.

After completion of the reaction, the reaction mixture was poured into water and subjected to extraction with methylene chloride. The extract was washed with water, dried over anhydrous sodium sulfate, and concentrated under reduced pressure. The resulting residue was purified through silica gel column chromatography with a developing solvent (ethyl acetate:hexane=1:3) to obtain 5.7 g of 2-amino-6-benzylthiopyridine having a melting point of 65° to 66° C.

2) 5.75 g of 2-amino-6-benzylthiopyridine and 86 ml of tetrahydrofuran was mixed together and further admixed with 1.67 g of powdery potassium hydroxide, followed by agitation thereof at room temperature. The resulting mixture was cooled with ice. 6.10 g of methanesulfonyl chloride was added dropwise to the ice-cooled mixture, followed by reaction under agitation at room temperature over one night.

After completion of the reaction, the reaction mixture was poured into water and subjected to extraction with methylene chloride. The exctract was dried over anhydrous sodium sulfate and concentrated under reduced pressure. The resulting residue was purified through silica gel column chromatography with a developing solvent (ethyl acetate:hexane= 1:1) to obtain 1.5 g of N-(6-benzylthiopyridin-2-yl)methanesulfonamide having a melting point of 123° to 125° C.

3) 1.0 g of N-(6-benzylthiopyridin-2-yl)methanesulfonamide obtained in the above step 2) was mixed with 15 ml of tetrahydrofuran. The resulting mixture was cooled with ice and admixed with 0.15 g of 60 wt % sodium hydride, followed by agitation thereof at room temperature. Thereafter, 3.56 g of ethyl iodide was added to the mixture. The resulting mixture was heated up and reacted under reflux over one night.

After completion of the reaction, the reaction mixture was poured into water, weakly acidified with hydrochloric acid, and subjected to extraction with methylene chloride. The extract was dried over anhydrous sodium sulfate and concentrated under reduced pressure. The resulting residue was purified through silica gel column chromatography with a developing solvent (ethyl acetate:hexane=1:1) to obtain 0.8 g of white crystals of N-(6-benzylthiopyridin-2-yl)-N-ethylmethanesulfonamide.

4) 0.8 g of N-(6-benzylthiopyridin-2-yl)-N-ethylmethanesulfonamide obtained in the above step 3) was mixed with 10 ml of acetic acid and 10 ml of water. The resulting mixture was cooled to −5° to 0° C. Thereafter, chlorine gas was introduced into the cooled mixture to effect a reaction.

After completion of the reaction, the reaction mixture was poured into water and subjected to extraction with methylene chloride. The extract was washed with water and dried over anhydrous sodium sulfate, followed by introduction thereinto of ammonia gas to effect a reaction at room temperature for one hour.

After completion of the reaction, the reaction mixture was filtered. The filtrate was concentrated under reduced pressure and allowed to stand. Thereafter, the solidified residue was washed with ethyl acetate and n-hexane to obtain 0.62 g of 6-[(N-ethyl-N-methylsulfonyl)amino]-2-pyridinesulfonamide (Intermediate No. 2 in Table 1 which will be given later) having a melting point of 140° to 143° C.

5) 0.20 g of 6-[(N-ethyl-N-methylsulfonyl)amino]-2-pyridinesulfonamide obtained in the above step 4) was mixed with 0.20 g of phenyl (4,6-dimethoxypyrimidin-2-yl)carbamate and 7 ml of acetonitrile. The resulting mixture was further admixed and reacted with 0.11 g of 1,8-diazabicyclo [5.4.0]-7-undecene at room temperature for one hour.

After completion of the reaction, the reaction mixture was poured into water and weakly acidified with hydrochloric acid. The resulting solid substance was filtered off, washed with water, and dried to obtain 0.25 g of the desired product (Compound No. α-2) having a melting point of 145° to 147° C.

SYNTHESIS EXAMPLE 2

Synthesis of 6-[(N-ethyl-N-ethylsulfonyl)amino]-N-[[(4,6-dimethoxypyrimidin-2-yl)amino] -carbonyl]-2-pyridinesulfonamide (Compound No. α-18 in Table 2-α which will be given later)

1) 2.0 g of 2-amino-6-benzylthiopyridine and 30 ml of tetrahydrofuran was mixed together and further admixed with 0.52 g of powdery potassium hydroxide, followed by agitation thereof at room temperature. The resulting mixture was cooled with ice. 2.38 g of ethanesulfonyl chloride was added dropwise to the ice-cooled mixture, followed by reaction under agitation at room temperature for 30 minutes.

After completion of the reaction, the reaction mixture was poured into water and subjected to extraction with methylene chloride. The extract was dried over anhydrous sodium sulfate and concentrated under reduced pressure. The resulting residue was purified through silica gel column chromatography with a developing solvent (ethyl acetate:hexane= 1:1) to obtain 0.90 g of N-(6-benzylthiopyridin-2-yl)ethanesulfonamide having a melting point of 87° to 92° C.

2) 0.85 g of N-(6-benzylthiopyridin-2-yl)ethanesulfonamide obtained in the above step 1) was mixed with 15 ml of tetrahydrofuran. The resulting mixture was cooled with ice and admixed with 0.13 g of 60 wt % sodium hydride, followed by agitation thereof at room temperature. Thereafter, 2.0 g of ethyl iodide was added to the mixture. The resulting mixture was heated up and reacted under reflux for 1.5 hours.

After completion of the reaction, the reaction mixture was poured into water and subjected to extraction with methylene chloride. The extract was dried over anhydrous sodium sulfate and concentrated under reduced pressure. The resulting residue was purified through silica gel column chromatography with a developing solvent (ethyl acetate:hexane= 1:1) to obtain 0.75 g of oily N-(6-benzylthiopyridin-2-yl)-N-ethylethanesulfonamide.

3) 0.75 g of N-(6-benzylthiopyridin-2-yl)-N-ethylethanesulfonamide obtained in the above step 2) was mixed with 20 ml of acetic acid and 15 ml of water. The resulting mixture was cooled to −5° to 0° C. Thereafter, the chlorine gas was introduced into the cooled mixture to effect a reaction.

After completion of the reaction, the reaction mixture was poured into water and subjected to extraction with methylene chloride. The extract was washed with water and dried over anhydrous sodium sulfate, followed by introduction thereinto of ammonia gas to effect a reaction at room temperature for one hour.

After completion of the reaction, the reaction mixture was filtered. The filtrate was concentrated under reduced pressure and allowed to stand. Thereafter, the solidified residue was washed with ethyl acetate and n-hexane to obtain 0.60 g of 6-[(N-ethyl-N-ethylsulfonyl)amino]-2-pyridinesulfonamide (Intermediate No. 17 in Table 1 which will be given later) having a melting point of 115° to 118° C.

4) 0.21 g of 6-[(N-ethyl-N-ethylsulfonyl)amino]-2-pyridinesulfonamide obtained in the above step 3) was mixed with 0.20 g of phenyl (4,6-dimethoxypyrimidin-2-yl)carbamate and 7 ml of acetonitrile. The resulting mixture was further admixed and reacted with 0.11 g of 1,8-diazabicyclo [5.4.0]-7-undecene at room temperature for 30 minutes.

After completion of the reaction, the reaction mixture was poured into water and weakly acidified with hydrochloric acid. The resulting solid substance was filtered off, washed with water, and dried to obtain 0.25 g of the desired product (Compound No. α-18) having a melting point of 165° to 170° C.

SYNTHESIS EXAMPLE 3

Synthesis of 6-[(N-ethyl-N-isopropylsulfonyl)amino]-N-[ [(4,6-dimethoxypyrimidin-2-yl)amino]carbonyl]- 2-pyridinesulfonamide (Compound No. α-22 in Table 2-α which will be given later)

1) 12 g of 2-benzylthio-6-bromopyridine, 70 ml of a 40 wt % aqueous solution of ethylamine, and a catalytic amount of cuprous chloride were mixed together and reacted in an autoclave at 180° C. for 4 hours.

After completion of the reaction, the reaction mixture was poured into water and subjected to extraction with methylene chloride. The extract was washed with water, dried over anhydrous sodium sulfate, and concentrated under reduced pressure. The resulting residue was purified through silica gel column chromatography with a developing solvent (ethyl acetate:hexane=1:10) to obtain 5.5 g of oily 2-benzylthio-6-ethylaminopyridine.

2) 2.0 g of 2-benzylthio-6-ethylaminopyridine obtained in the above step 1) was mixed and reacted with 2.33 g of isopropylsulfonyl chloride under agitation at 80° to 100° C. for one night.

After completion of the reaction, methylene chloride was added to the reaction mixture. The resulting mixture was washed with water, dried over anhydrous sodium sulfate, and concentrated under reduced pressure. The resulting residue was purified through silica gel column chromatography with a developing solvent (ethyl acetate:hexane=1:10) to obtain 0.20 g of oily N-(6-benzylthiopyridin-2-yl)-N-ethylisopropylsulfonamide. $^1$NMR (400 MHz, CDCl$_3$) δ (ppm): 1.14 (3H, t, J=7.0 Hz), 1.25 (6H, d, J=6.4 Hz), 3.27 (1H, m,), 3.99 (2H, q, J=7.0 Hz), 4.38 (2H, s), 6.99 (1H, d, J=8.2 Hz), 7.15 (1H, d, J=8.2 Hz), 7.20–7.28 (3H, m,), 7.36 (2H, d, J=6.8 Hz), 7.46 (1H, t, J=8.2 Hz)

3) 0.20 g of N-(6-benzylthiopyridin-2-yl)-N-ethylisopropylsulfonamide obtained in the above step 2) was mixed with 25 ml of acetic acid and 20 ml of water. The resulting mixture was cooled to −5° to 0° C. Chlorine gas was introduced into the cooled mixture to effect a reaction.

After completion of the reaction, the reaction mixture was poured into water and subjected to extraction with methylene chloride. The extract was washed with water and dried over anhydrous sodium sulfate, followed by introduction thereinto of ammonia gas to effect a reaction at room temperature for 30 minutes.

After completion of the reaction, the reaction mixture was filtered. The filtrate was concentrated under reduced pressure. The resulting residue was purified through silica gel column chromatography with a developing solvent (ethyl acetate:hexane=3:1) to obtain 0.12 g of 6-[(N-ethyl-N-isopropylsulfonyl)amino]-2-pyridinesulfonamide (Intermediate No. 21 in Table 1 which will be given later) having a melting point of 107° to 109° C.

4) 0.12 g of 6-[(N-ethyl-N-isopropylsulfonyl)amino]-2-pyridinesulfonamide obtained in the above step 3) was mixed with 0.11 g of phenyl (4,6-dimethoxypyrimidin-2-yl)carbamate and 7 ml of acetonitrile and further admixed with 59 mg of 1,8-diazabicyclo[5.4.0]-7-undecene to effect a reaction at room temperature for 30 minutes.

After completion of the reaction, the reaction mixture was poured into water, weakly acidified with hydrochloric acid, and subjected to extraction with methylene chloride. The extract was dried over anhydrous sodium sulfate and concentrated under reduced pressure. The resulting residue was purified through silica gel column chromatography with a developing solvent (ethyl acetate:hexane=4:1) to obtain 0.11 g of the desired product (Compound No. α-22) having a melting point of 163° to 166° C.

SYNTHESIS EXAMPLE 4

Synthesis of 6-[(N-Ethyl-N-isopropylsulfonyl)amino]-N-[[(4-methoxy-6-methyltriazin-2-yl)amino]carbonyl-2-pyridinesulfonamide (Compound No. β-1 in Table 2-β which will be given later)

1) A mixture of 10 g of 2-benzylthio-6-bromopyridine, 70 ml of a 40% ethylamine aqueous solution, and a catalytic amount of cuprous chloride was allowed to react in an autoclave at 150° C. for 10 hours. After completion of the reaction, the reaction mixture was poured into water and extracted with methylene chloride. The extract was washed with water, dried over anhydrous sodium sulfate, and concentrated under reduced pressure. The residue was purified by silica gel column chromatography (developing solvent: ethyl acetate/hexane=1/4 by volume) to obtain 4.7 g of 2-benzylthio-6-ethylaminopyridine as an oily substance.

2) To a mixture of 3.16 g of the 2-benzylthio-6-ethylaminopyridine obtained in 1) above and 30 ml of tetrahydrofuran was added dropwise 9.4 ml of a 1.65 mol/l hexane solution of n-butyl lithium at −10° to 0° C. in a nitrogen stream. To the reaction mixture was added 1.84 g of isopropylsulfonyl chloride at 0° to 15° C., followed by reacting for 0.5 hour. After completion of the reaction, the reaction mixture was poured into water, made weakly acidic with hydrochloric acid, and extracted with methylene chloride. The extract was dried over anhydrous sodium sulfate, followed by concentration under reduced pressure. The residue was purified by silica gel column chromatography (developing solvent: ethyl acetate/hexane=1/19 by volume) to obtain 0.77 g of N-(6-benzylthiopyridin-2-yl)-N-ethylisopropylsulfonamide as an oily substance.

3) A mixture of 0.75 g of the N-(6-benzylthiopyridin-2-yl)-N-ethylisopropylsulfonamide obtained in 2) above, 20ml of acetic acid, and 15 ml of water was cooled to −5° to 0° C., and chlorine gas was introduced therein to conduct a reaction. After completion of the reaction, the reaction mixture was poured into water, extracted with methylene chloride, washed with water, and dried over anhydrous sodium sulfate. Ammonia gas was introduced into the reaction mixture to further conduct a reaction at room temperature for 1 hour. After the reaction, the reaction mixture was filtered, and the filtrate was concentrated under reduced pressure. The residue was purified by silica gel column chromatography (developing solvent: ethyl acetate/hexane= 2/1 by volume) to obtain 0.50 g of 6-[(N-ethyl-N-isopropylsulfonyl)amino]-2-pyridinesulfonamide (Intermediate No. 21 in Table 1 which will be given later) having a melting point of 107° to 109° C.

4) To a mixture of 0.10 g of 6-[(N-ethyl-N-isopropylsulfonyl)amino]-2-pyridinesulfonamide obtained in 3) above, 0.089 g of phenyl (4-methoxy-6-methyltriazin-2-yl)carbamate, and 7 ml of acetonitrile was added 0.050 g of 1,8-diazabicyclo[5.4.0]-7-undecene, and the mixture was allowed to react at room temperature for hour. After completion of the reaction, the reaction mixture was poured into water and made weakly acidic with hydrochloric acid. The thus precipitated solid was collected by filtration, washed with water, and dried to obtain 0.13 g of the titled compound having a melting point of 146° to 148° C.

SYNTHESIS EXAMPLE 5

Synthesis of 6-[(N-Ethyl-N-isopropylsulfonyl)amino]-N-[[(4,6-dimethoxytriazin-2-yl)amino] carbonyl]-2-pyridinesulfonamide (Compound No. β-2 in Table 2-β which will be given later).

To a mixture of 0.15 g of the 6-[(N-ethyl-N-isopropylsulfonyl)amino]-2-pyridinesulfonamide obtained in Synthesis Example 1–3), 0.135 g of phenyl (4,6-dimethoxytriazin-2-yl)carbamate, and 7 ml of acetonitrile was added 0.074 g of 1,8-diazabicyclo[5.4.0]-7-undecene, and the mixture was allowed to react at room temperature for 1 hour. After the reaction, the reaction mixture was poured into water and made weakly acidic with hydrochloric acid. The thus precipitated solid was collected by filtration, washed with water, and dried to obtain 0.20 g of the titled compound having a melting point of 144° to 146° C.

SYNTHESIS EXAMPLE 6

Synthesis of 6-[[N-(1-Chloroethylsulfonyl)-N-ethyl]amino]-N-[[(4-methoxy-6-methyltriazin- 2-yl)amino]carbonyl]-2-pyridinesulfonamide (Compound No. β-54 in Table 2-β which will be given later)

1) A mixture-of 10 g of 2-benzylthio-6-bromopyridine, 70 ml of a 40% ethylamine aqueous solution, and a catalytic amount of cuprous chloride was allowed to react in an autoclave at 180° C. for 4 hours. After completion of the reaction, the reaction mixture was poured into water and extracted with methylene chloride. The extract was washed with water, dried over anhydrous sodium sulfate, and concentrated under reduced pressure. The residue was purified by silica gel column chromatography (developing solvent: ethyl acetate/hexane=1/19 by volume) to obtain 5.9 g of 2-benzylthio-6-ethylaminopyridine as an oily substance.

2) To a mixture of 3 g of the 2-benzylthio-6-ethylaminopyridine obtained in 1) above and 30 ml of tetrahydrofuran was added dropwise 8.1 ml of a 1.65 mol/l hexane solution of n-butyl lithium at −10° to 0° C. in a nitrogen stream. To the reaction mixture was added 1.9 g of ethylsulfonyl chloride at 0° to 15° C., followed by reacting for 0.5 hour. After completion of the reaction, the reaction mixture was poured into water and extracted with methylene chloride. The extract was dried over anhydrous sodium sulfate, followed by concentration under reduced pressure. The residue was purified by silica gel column chromatography (developing solvent: ethyl acetate/hexane=1/19 by volume) to obtain 1.39 g of N-(6-benzylthiopyridin-2-yl)-N-ethyl(1-chloroethyl)sulfonamide having a melting point of 50° to 52° C. The intermediate was found to be a racemic modification.

3) A mixture of 1.39 g of the N-(6-benzylthiopyridin-2-yl)-N-ethyl(1-chloroethyl)sulfonamide obtained in 2) above, 30 ml of acetic acid, and 15 ml of water was cooled to −5° to 0° C., and chlorine gas was introduced therein to conduct a reaction. After completion of the reaction, the reaction mixture was poured into water, extracted with methylene chloride, washed with water, and dried over anhydrous sodium sulfate. Ammonia gas was introduced into the reaction mixture to further conduct a reaction at room temperature for 1 hour. After the reaction, the reaction mixture was filtered, and the filtrate was concentrated under reduced pressure. The residue was purified by silica gel column chromatography (developing solvent: ethyl acetate/hexane=

2/1 by volume) to obtain 1.11 g of 6-[[N-(1-chloroethylsulfonyl)-N-ethyl]amino]- 2-pyridinesulfonamide (Intermediate No. 90 in Table 1 which will be given later) having a melting point of 101° to 103° C. The intermediate was found to be a racemic modification.

4) To a mixture of 0.39 g of the 5-[[N-(1-chloroethylsulfonyl)-N-ethyl]amino]-2-pyridinesulfonamide obtained in 3) above, 0.31 g of phenyl (4-methoxy6-methyltriazin-2-yl)carbamate, and 10 ml of acetonitrile was added 0.18 g of 1,8-diazabicyclo[5.4.0]-7-undecene, and the mixture was allowed to react at room temperature for 1 hour. After completion of the reaction, the reaction mixture was poured into water and made weakly acidic with hydrochloric acid. The thus precipitated solid was collected by filtration, washed with water, and dried to obtain 0.58 g of the desired compound having a melting point of 155° to 157° C. The product was found to be a racemic modification.

SYNTHESIS EXAMPLE 7

Synthesis of 6-[(N-Dichloromethylsulfonyl-N-ethyl)amino]-N-[[(4,6-dimethoxytriazin-2-yl) amino]carbonyl]-2-pyridinesulfonamide (Compound No. β-57 in Table 2-β which will be given later)

1) To a mixture of 6 g of 2-benzylthio-6-ethylaminopyridine and 60 ml of tetrahydrofuran was added dropwise 17.3 ml of a 1.65 mol/l hexane solution of n-butyl lithium at −10° to 0° C. in a nitrogen stream. To the reaction mixture was added 3.4 g of methysulfonyl chloride at 0° to 15° C., followed by reacting for 0.5 hour. After completion of the reaction, the reaction mixture was poured into water, made weakly acidic with hydrochloric acid, and extracted with methylene chloride. The extract was dried over anhydrous sodium sulfate, followed by concentration under reduced pressure. The residue was purified by silica gel column chromatography (developing solvent; ethyl acetate/hexane=1/19 by volume) to obtain 3.4 g of N-(6-benzylthiopyridine-2-yl)-N-ethylmethylsulfonamide as an orange crystal.

$^1$H-NMR (60 MHz, CDCl$_3$) δ (ppm): 1.12 (3H, t, J=7.3 Hz), 2.84 (3H, s), 3.85 (2H, q, J=7.3 Hz), 4.34 (2H, s), 6.8–7.6 (8H, m)

2) To a mixture of 3.6 g of N-(6-benzylthiopyridin-2-yl)-N-ethylmethylsulfonamide and 50 ml of tetrahydrofuran was added dropwise 8 ml of a 1.65 mol/l hexane solution of n-butyl lithium at −30 to −20° C. in a nitrogen stream. Then, 1.8 g of N-chlorosuccinimide was added thereto at −30 to −20° C., followed by reacting for 1 hour. After completion of the reaction, the reaction mixture was poured into water and extracted with methylene chloride. The extract was dried over anhydrous sodium sulfate. followed by concentration under reduced pressure. The residue was purified by silica gel column chromatography (developing solvent: ethyl acetate/hexane=1/9 by volume) to obtain 0.7 g of N-(6-benzylthiopyridin-2-yl)-N-ethyldichloromethylsulfonamide as an oily substance.

$^1$H-NMR (60 MHz, CDCl$_3$) δ (ppm): 1.17 (3H, t, J=7.3 Hz), 4.00 (2H, q, J=7.3 Hz), 4.37 (2H, s), 6.53 (1H, s), 6.8–7.6 (8H, m)

3) A mixture of 1.4 g of N-(6-benzylthiopyridin-2-yl)-N-ethyldichloromethylsulfonamide, 20 ml of methylene chloride, 2.5 ml of concentrated hydrochloric acid, and 10 ml of water was cooled to −5° to 0° C., and 8 ml of a sodium hypochlorite solution (active chlorine: 8.5 to 13.5%) was added thereto dropwise to conduct a reaction. After completion of the reaction, the reaction mixture was poured into water, extracted with methylene chloride, washed with water, and dried over anhydrous sodium sulfate. Ammonia gas was introduced into the reaction mixture to futher conduct a reaction at room temperature for 1 hour. After the reaction, the reaction mixture was filtered, and the filtrate was concentrated under reduced pressure. The residue was purified by silica gel column chromatography (developing solvent: ethyl acetate/hexane=2/1 by volume) to obtain 0.8 g of 6-[(N-dichloromethylsulfonyl-N-ethyl)amino]-2-pyridinesulfonamide (Intermediate No. 91 in Table 1 which will be given later) having a melting point of 148 to 150° C.

4) To a mixture of 0.17 g of the 6-[(N-dichloromethylsulfonyl-N-ethyl)amino]-2-pyridinesulfonamide obtained in 3) above, 0.14 g of phenyl (4,6-dimethoxytriazin-2-yl)carbamate, and 10 ml of acetonitrile was added 0.08 g of 1,8-diazabicyclo[5.4.0]-7-undecene, and the mixture was allowed to react at room temperature for 1 hour. After completion of the reaction, the reaction mixture was poured into water and made weakly acidic with hydrochloric acid. The thus precipitated solid was collected by filtration, washed with water, and dried to obtain 0.18 g of the desired compound having a melting point of 157° to 159° C.

Representative examples of the intermediate represented by the general formula (II-1) which were prepared in substantially the same manner as described above are listed in Table 1, while representative examples of the substituted pyridinesulfonamide compound of the present invention represented by the general formula (I) which were prepared in substantially the same manner as described above are listed in Table 2-α (when A is CH) and Table 2-β (when A is N).

TABLE 1

| Intermediate No. | R$_1$ | R$_2$ | Physical Properties m.p. (°C.) |
|---|---|---|---|
| 1 | CH$_3$ | CH$_3$ | 118–119 |
| 2 | CH$_3$ | C$_2$H$_5$ | 140–143 |
| 3 | CH$_3$ | n-C$_3$H$_7$ | 100–104 |
| 4 | C$_2$H$_5$ | CH$_3$ | 86–90 |
| 5 | CF$_3$ | CH$_3$ | 195–198 |
| 6 | CF$_3$ | C$_2$H$_5$ | 148–151 |
| 7 | CF$_3$ | n-C$_3$H$_7$ | 142–145 |
| 8 | CF$_3$ | n-C$_4$H$_9$ | 138–140 |
| 9 | CH$_3$ | iso-C$_3$H$_7$ | 179–181 |
| 10 | CF$_3$ | iso-C$_3$H$_7$ | |
| 11 | iso-C$_3$H$_7$ | CH$_3$ | 130–133 |
| 12 | cyclopropyl | CH$_3$ | 132–134 |
| 13 | CH$_3$ | cyclopropyl | |
| 14 | CH$_3$ | CH$_2$OCH$_3$ | 147–153 |
| 15 | C$_2$H$_5$ | CH$_2$OCH$_3$ | 110–112 |
| 16 | n-C$_4$H$_9$ | n-C$_4$H$_9$ | oil substance |
| 17 | C$_2$H$_5$ | C$_2$H$_5$ | 115–118 |
| 18 | C$_2$H$_5$ | n-C$_3$H$_7$ | 111–115 |
| 19 | n-C$_3$H$_7$ | CH$_3$ | oily substance |
| 20 | n-C$_3$H$_7$ | C$_2$H$_5$ | 125–128 |
| 21 | iso-C$_3$H$_7$ | C$_2$H$_5$ | 107–109 |
| 22 | n-C$_4$H$_9$ | C$_2$H$_5$ | 70–73 |
| 23 | tert-C$_4$H$_9$ | C$_2$H$_5$ | |
| 24 | n-C$_6$H$_{13}$ | C$_2$H$_5$ | |
| 25 | CH$_2$CF3 | C$_2$H$_5$ | 108–109 |
| 26 | (CH$_2$)$_3$Cl | C$_2$H$_5$ | oily substance |
| 27 | (CH$_2$)$_3$CF$_3$ | C$_2$H$_5$ | |
| 28 | C$_2$H$_5$OC$_2$H$_5$ | C$_2$H$_5$ | oily substance |
| 29 | CH(CH$_3$)CH$_2$OC$_2$H$_5$ | C$_2$H$_5$ | |
| 30 | CH═CH$_2$ | CH$_3$ | 108–113 |
| 31 | CH═CH$_2$ | C$_2$H$_5$ | 75–79 |
| 32 | CH═CHCF$_3$ | C$_2$H$_5$ | |
| 33 | cyclohexyl | C$_2$H$_5$ | 123–124 |
| 34 | cyclopropyl | C$_2$H$_5$ | 137–139 |
| 35 | C$_2$H$_5$ | cyclopropyl | |
| 36 | cyclopentyl | C$_2$H$_5$ | oily substance |

TABLE 1-continued

| Intermediate No. | R₁ | R₂ | Physical Properties m.p. (°C.) |
|---|---|---|---|
| 37 |  | $CH_3$ | 96–99 |
| 38 |  | $C_2H_5$ | oily substance |
| 39 |  | $CH_3$ | oily substance |
| 40 |  | $C_2H_5$ | oily substance |
| 41 |  | $CH_3$ | oily substance |
| 42 |  | $C_2H_5$ | 98–100 |
| 43 |  | $C_2H_5$ | |
| 44 | 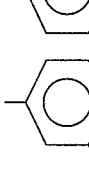 | $C_2H_5$ | 185–188 |
| 45 | sec-$C_4H_9$ | $CH_3$ | 95–96 |
| 46 | sec-$C_4H_9$ | $C_2H_5$ | oily substance |
| 47 | sec-$C_4H_9$ | n-$C_3H_7$ | 103–105 |
| 48 | sec-$C_4H_9$ | iso-$C_3H_7$ | 111–119 |
| 49 | iso-$C_3H_7$ | n-$C_3H_7$ | oily substance |
| 50 | iso-$C_4H_9$ | $C_2H_5$ | oily substance |
| 51 | n-$C_4H_9$ | $CH_3$ | oily substance |
| 52 | $(CH_2)_2CH(CH_3)_2$ | $C_2H_5$ | oily substance |
| 53 | $(CH_2)_2CH(CH_3)_2$ | $CH_3$ | oily substance |
| 54 | $CH_3$ | $CHF_2$ | 126–128 |
| 55 | $C_2H_5$ | $CHF_2$ | 106–109 |
| 56 | cyclohexyl | $CH_3$ | oily substance |
| 57 | tert-$C_4H_9$ | $CH_3$ | |
| 58 | $CH_3$ | $CH_2CF_3$ | |
| 59 | $C_2H_5$ | $CH_2CF_3$ | |
| 60 | iso-$C_3H_7$ | $CH_2CF_3$ | |
| 61 | $C_2H_5$ | iso-$C_3H_7$ | 183–185 |
| 62 | n-$C_3H_7$ | iso-$C_3H_7$ | |
| 63 | cyclopropyl | n-$C_3H_7$ | |
| 64 | n-$C_3H_7$ | cyclopropyl | |
| 65 | $CH_3$ | n-$C_4H_9$ | 98–103 |
| 66 | $C_2H_5$ | n-$C_4H_9$ | 104–108 |
| 67 | n-$C_3H_7$ | n-$C_4H_9$ | 108–110 |
| 68 | iso-$C_3H_7$ | n-$C_4H_9$ | 119–121 |
| 69 | $CH_3$ | sec-$C_4H_9$ | 181–182 |
| 70 | $C_2H_5$ | sec-$C_4H_9$ | |
| 71 | n-$C_3H_7$ | sec-$C_4H_9$ | 138–143 |
| 72 | iso-$C_3H_7$ | sec-$C_4H_9$ | |
| 73 | $CH_3$ | iso-$C_4H_9$ | 178–180 |
| 74 | $C_2H_5$ | iso-$C_4H_9$ | 174–177 |
| 75 | n-$C_3H_7$ | iso-$C_4H_9$ | 140–142 |
| 76 | iso-$C_3H_7$ | iso-$C_4H_9$ | 134–135 |
| 77 | n-$C_3H_7$ | n-$C_3H_7$ | 115–117 |
| 78 | iso-$C_3H_7$ | iso-$C_3H_7$ | 145–146 |
| 79 | cyclopropyl | iso-$C_3H_7$ | |
| 80 | iso-$C_4H_9$ | $CH_3$ | oily substance |
| 81 | cyclobutyl | $CH_3$ | 142–144 |
| 82 | cyclobutyl | $C_2H_5$ | oily substance |
| 83 | cyclobutyl | n-$C_3H_7$ | |
| 84 | cyclobutyl | iso-$C_3H_7$ | |
| 85 | iso-$C_4H_9$ | n-$C_3H_7$ | 117–119 |
| 86 | iso-$C_4H_9$ | iso-$C_3H_7$ | 161–169 |
| 87 | n-$C_4H_9$ | n-$C_3H_7$ | oily substance |
| 88 | n-$C_4H_9$ | iso-$C_3H_7$ | 115–124 |
| 89 | $CH_2CF_3$ | $CH_2OCH_3$ | 133–135 |
| 90 | $CH_3CH(Cl)$ | $C_2H_5$ | 101–103 |
| 91 | $CH_2Cl_2$ | $C_2H_5$ | 148–150 |
| 92 | $CH_2CH(F)$ | $C_2H_5$ | 113–116 |
| 93 | $CH_2Cl$ | $C_2H_5$ | oily substance |
| 94 | $CH_3CH(CF_3)$ | $C_2H_5$ | |
| 95 | $CH_3CH(CHF_2)$ | $C_2H_5$ | |
| 96 | $CH_3CH(CH_2F)$ | $C_2H_5$ | |
| 97 | $CH_2Cl$ | $CH_3$ | |
| 98 | $CH_2Cl$ | n-$C_3H_7$ | |
| 99 | $CHF_2$ | $C_2H_5$ | |
| 100 | $CH_2F$ | $C_2H_5$ | |
| 101 | $CH_3CF_2$ | $C_2H_5$ | |
| 102 | $CH_3CH(Cl)$ | $CH_2CF_3$ | |
| 103 | $CH_3CH(Cl)$ | $CH_2CH_2F$ | |
| 104 | $CH_3CH(Cl)$ | $CH_2CH_2Cl$ | |
| 105 | $CH_3CH(Br)$ | $C_2H_5$ | oily substance |
| 106 | iso-$C_4H_9$ | sec-$C_4H_9$ | oily substance |
| 107 | sec-$C_4H_9$ | sec-$C_4H_9$ | 141–143 |
| 108 | n-$C_4H_9$ | iso-$C_4H_9$ | oily substance |
| 109 | sec-$C_4H_9$ | iso-$C_4H_9$ | oily substance |
| 110 | n-$C_4H_9$ | sec-$C_4H_9$ | oily substance |
| 111 | $CH_3CH(Cl)$ | $CH_3$ | 132–135 |
| 112 | $CH_3CH(Cl)$ | n-$C_3H_7$ | oily substance |
| 113 | $(CH_3)_2CCl$ | $C_2H_5$ | 159–161 |
| 114 | $CH_3CH_2CH(Cl)$ | $C_2H_5$ | oily substance |
| 115 | $CBr_3$ | $CH_3$ | 190–192 |
| 116 | $CBr_3$ | $C_2H_5$ | 143–145 |
| 117 | $CCl_3$ | $C_2H_5$ | |
| 118 | $CH_3CH(Cl)$ | iso-$C_3H_7$ | 146–148 |
| 119 | $CH_2CF_3$ | n-$C_3H_7$ | 105–107 |
| 120 | $CF_3$ | $CH_2OCH_3$ | 103–106 |
| 121 | $CH_3CH(OCH_3)$ | $CH_3$ | |
| 122 | $CH_3CH(OCH_3)$ | $C_2H_5$ | |
| 123 | $CH_3CH(OC_2H_5)$ | $CH_3$ | |
| 124 | $CH_3CH(OC_2H_5)$ | $C_2H_5$ | |
| 125 | $CH_3$ | $OCH_3$ | 93–96 |
| 126 | $C_2H_5$ | $OCH_3$ | viscous oily substance |
| 127 | iso-$C_3H_7$ | $OCH_3$ | viscous oily substance |
| 128 | n-$C_4H_9$ | $OCH_3$ | |
| 129 | $CH_3$ | $OC_2H_5$ | |
| 130 | n-$C_3H_7$ | $OC_2H_5$ | |
| 131 | $CF_3$ | $OCH_3$ | |
| 132 | $CF_3$ | $OC_2H_5$ | |
| 133 | $CH_2CF_3$ | $OCH_3$ | |

TABLE 2-α

| Compound No. | $R_1$ | $R_2$ | x | y | Physical Properties m.p. (°C.) |
|---|---|---|---|---|---|
| α-1 | $CH_3$ | $CH_3$ | $OCH_3$ | $OCH_3$ | 176–177 |
| α-2 | $CH_3$ | $C_2H_5$ | $OCH_3$ | $OCH_3$ | 145–147 |
| α-3 | $CH_3$ | $n$-$C_3H_7$ | $OCH_3$ | $OCH_3$ | 85–88 |
| α-4 | $C_2H_5$ | $CH_3$ | $OCH_3$ | $OCH_3$ | 161–163 |
| α-5 | $CF_3$ | $CH_3$ | $OCH_3$ | $OCH_3$ | viscous substance |
| α-6 | $CF_3$ | $C_2H_5$ | $OCH_3$ | $OCH_3$ | 179–180 |
| α-7 | $CF_3$ | $n$-$C_3H_7$ | $OCH_3$ | $OCH_3$ | 159–161 |
| α-8 | $CF_3$ | $n$-$C_4H_9$ | $OCH_3$ | $OCH_3$ | 116–118 |
| α-9 | $CH_3$ | iso-$C_3H_7$ | $OCH_3$ | $OCH_3$ | 132–138 |
| α-10 | $CF_3$ | iso-$C_3H_7$ | $OCH_3$ | $OCH_3$ | |
| α-11 | iso-$C_3H_7$ | $CH_3$ | $OCH_3$ | $OCH_3$ | 143–146 |
| α-12 | cyclopropyl | $CH_3$ | $OCH_3$ | $OCH_3$ | 164–168 |
| α-13 | $CH_3$ | cyclopropyl | $OCH_3$ | $OCH_3$ | |
| α-14 | $CH_3$ | $C_2H_5$ | $CH_3$ | $OCH_3$ | |
| α-15 | $CH_3$ | $CH_2OCH_3$ | $OCH_3$ | $OCH_3$ | |
| α-16 | $C_2H_5$ | $CH_2OCH_3$ | $OCH_3$ | $OCH_3$ | |
| α-17 | $n$-$C_4H_9$ | $n$-$C_4H_9$ | $OCH_3$ | $OCH_3$ | |
| α-18 | $C_2H_5$ | $C_2H_5$ | $OCH_3$ | $OCH_3$ | 165–170 |
| α-19 | $C_2H_5$ | $n$-$C_3H_7$ | $OCH_3$ | $OCH_3$ | 140–143 |
| α-20 | $n$-$C_3H_7$ | $CH_3$ | $OCH_3$ | $OCH_3$ | 175–178 |
| α-21 | $n$-$C_3H_7$ | $C_2H_5$ | $OCH_3$ | $OCH_3$ | 151–154 |
| α-22 | iso-$C_3H_7$ | $C_2H_5$ | $OCH_3$ | $OCH_3$ | 163–166 |
| α-23 | $n$-$C_4H_9$ | $C_2H_5$ | $OCH_3$ | $OCH_3$ | 155–158 |
| α-24 | tert-$C_4H_9$ | $C_2H_5$ | $OCH_3$ | $OCH_3$ | |
| α-25 | $n$-$C_6H_{13}$ | $C_2H_5$ | $OCH_3$ | $OCH_3$ | |
| α-26 | $CH_2CF_3$ | $C_2H_5$ | $OCH_3$ | $OCH_3$ | 184–185 |
| α-27 | $(CH_2)_3Cl$ | $C_2H_5$ | $OCH_3$ | $OCH_3$ | 156–159 |
| α-28 | $(CH_2)_3CF_3$ | $C_2H_5$ | $OCH_3$ | $OCH_3$ | |
| α-29 | $C_2H_5OC_2H_5$ | $C_2H_5$ | $OCH_3$ | $OCH_3$ | |
| α-30 | $CH(CH_3)CH_2OC_2H_5$ | $C_2H_5$ | $OCH_3$ | $OCH_3$ | |
| α-31 | $CH=CH_2$ | $CH_3$ | $OCH_3$ | $OCH_3$ | 150–152 |
| α-32 | $CH=CH_2$ | $C_2H_5$ | $OCH_3$ | $OCH_3$ | 145–148 |
| α-33 | $CH=CHCF_3$ | $C_2H_5$ | $OCH_3$ | $OCH_3$ | |
| α-34 | cyclohexyl | $C_2H_5$ | $OCH_3$ | $OCH_3$ | 148–149 |
| α-35 | cyclopropyl | $C_2H_5$ | $OCH_3$ | $OCH_3$ | 169–172 |
| α-36 | $C_2H_5$ | cyclopropyl | $OCH_3$ | $OCH_3$ | |
| α-37 | cyclopentyl | $C_2H_5$ | $OCH_3$ | $OCH_3$ | 135–138 |
| α-38 |  | $CH_3$ | $OCH_3$ | $OCH_3$ | 170–174 |
| α-39 |  | $C_2H_5$ | $OCH_3$ | $OCH_3$ | 142–145 |
| α-40 | 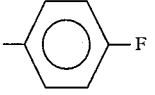 | $CH_3$ | $OCH_3$ | $OCH_3$ | 193–197 |
| α-41 | 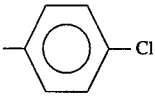 | $C_2H_5$ | $OCH_3$ | $OCH_3$ | 166–169 |
| α-42 | 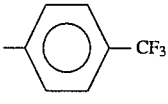 | $CH_3$ | $OCH_3$ | $OCH_3$ | 122–124 |
| α-43 | 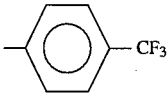 | $C_2H_5$ | $OCH_3$ | $OCH_3$ | 157–160 |
| α-44 | 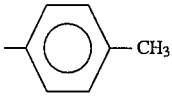 | $C_2H_5$ | $OCH_3$ | $OCH_3$ | |

TABLE 2-α-continued

| Compound No. | $R_1$ | $R_2$ | x | y | Physical Properties m.p. (°C.) |
|---|---|---|---|---|---|
| α-45 | (4-NO$_2$-phenyl) | C$_2$H$_5$ | OCH$_3$ | OCH$_3$ | 161–164 |
| α-46 | sec-C$_4$H$_9$ | CH$_3$ | OCH$_3$ | OCH$_3$ | 153–154 |
| α-47 | sec-C$_4$H$_9$ | C$_2$H$_5$ | OCH$_3$ | OCH$_3$ | 136–137 |
| α-48 | sec-C$_4$H$_9$ | n-C$_3$H$_7$ | OCH$_3$ | OCH$_3$ | |
| α-49 | sec-C$_4$H$_9$ | iso-C$_3$H$_7$ | OCH$_3$ | OCH$_3$ | |
| α-50 | iso-C$_3$H$_7$ | n-C$_3$H$_7$ | OCH$_3$ | OCH$_3$ | 163–166 |
| α-51 | iso-C$_4$H$_9$ | C$_2$H$_5$ | OCH$_3$ | OCH$_3$ | 150–153 |
| α-52 | n-C$_4$H$_9$ | CH$_3$ | OCH$_3$ | OCH$_3$ | 175–177 |
| α-53 | (CH$_2$)$_2$CH(CH$_3$)$_2$ | C$_2$H$_5$ | OCH$_3$ | OCH$_3$ | 139–140 |
| α-54 | (CH$_2$)$_2$CH(CH$_3$)$_2$ | CH$_3$ | OCH$_3$ | OCH$_3$ | 158–159 |
| α-55 | CH$_3$ | CHF$_2$ | OCH$_3$ | OCH$_3$ | 155–157 |
| α-56 | C$_2$H$_5$ | CHF$_2$ | OCH$_3$ | OCH$_3$ | 157–159 |
| α-57 | cyclohexyl | CH$_3$ | OCH$_3$ | OCH$_3$ | 164–165 |
| α-58 | (4-CF$_3$-phenyl) | CH$_3$ | CH$_3$ | CH$_3$ | 93–95 |
| α-59 | tert-C$_4$H$_9$ | CH$_3$ | OCH$_3$ | OCH$_3$ | |
| α-60 | CH$_3$ | CH$_2$CF$_3$ | OCH$_3$ | OCH$_3$ | |
| α-61 | C$_2$H$_5$ | CH$_2$CF$_3$ | OCH$_3$ | OCH$_3$ | |
| α-62 | iso-C$_3$H$_7$ | CH$_2$CF$_3$ | OCH$_3$ | OCH$_3$ | |
| α-63 | C$_2$H$_5$ | iso-C$_3$H$_7$ | OCH$_3$ | OCH$_3$ | 125–129 |
| α-64 | n-C$_3$H$_7$ | iso-C$_3$H$_7$ | OCH$_3$ | OCH$_3$ | |
| α-65 | cyclopropyl | n-C$_3$H$_7$ | OCH$_3$ | OCH$_3$ | |
| α-66 | n-C$_3$H$_7$ | cyclopropyl | OCH$_3$ | OCH$_3$ | |
| α-67 | CH$_3$ | n-C$_4$H$_9$ | OCH$_3$ | OCH$_3$ | |
| α-68 | C$_2$H$_5$ | n-C$_4$H$_9$ | OCH$_3$ | OCH$_3$ | |
| α-69 | n-C$_3$H$_7$ | n-C$_4$H$_9$ | OCH$_3$ | OCH$_3$ | |
| α-70 | iso-C$_3$H$_7$ | n-C$_4$H$_9$ | OCH$_3$ | OCH$_3$ | |
| α-71 | CH$_3$ | sec-C$_4$H$_9$ | OCH$_3$ | OCH$_3$ | |
| α-72 | C$_2$H$_5$ | sec-C$_4$H$_9$ | OCH$_3$ | OCH$_3$ | |
| α-73 | n-C$_3$H$_7$ | sec-C$_4$H$_9$ | OCH$_3$ | OCH$_3$ | |
| α-74 | iso-C$_3$H$_7$ | sec-C$_4$H$_9$ | OCH$_3$ | OCH$_3$ | |
| α-75 | CH$_3$ | iso-C$_4$H$_9$ | OCH$_3$ | OCH$_3$ | |
| α-76 | C$_2$H$_5$ | iso-C$_4$H$_9$ | OCH$_3$ | OCH$_3$ | |
| α-77 | n-C$_3$H$_7$ | iso-C$_4$H$_9$ | OCH$_3$ | OCH$_3$ | |
| α-78 | iso-C$_3$H$_7$ | iso-C$_4$H$_9$ | OCH$_3$ | OCH$_3$ | |
| α-79 | n-C$_3$H$_7$ | n-C$_3$H$_7$ | OCH$_3$ | OCH$_3$ | |
| α-80 | iso-C$_3$H$_7$ | iso-C$_3$H$_7$ | OCH$_3$ | OCH$_3$ | |
| α-81 | cyclopropyl | iso-C$_3$H$_7$ | OCH$_3$ | OCH$_3$ | |
| α-82 | iso-C$_4$H$_9$ | CH$_3$ | OCH$_3$ | OCH$_3$ | |
| α-83 | cyclobutyl | CH$_3$ | OCH$_3$ | OCH$_3$ | 167–169 |
| α-84 | cyclobutyl | C$_2$H$_5$ | OCH$_3$ | OCH$_3$ | 169–170 |
| α-85 | cyclobutyl | n-C$_3$H$_7$ | OCH$_3$ | OCH$_3$ | |
| α-86 | cyclobutyl | iso-C$_3$H$_7$ | OCH$_3$ | OCH$_3$ | |
| α-87 | iso-C$_4$H$_9$ | n-C$_3$H$_7$ | OCH$_3$ | OCH$_3$ | |
| α-88 | iso-C$_4$H$_9$ | iso-C$_3$H$_7$ | OCH$_3$ | OCH$_3$ | |
| α-89 | n-C$_4$H$_9$ | n-C$_3$H$_7$ | OCH$_3$ | OCH$_3$ | |
| α-90 | n-C$_4$H$_9$ | iso-C$_3$H$_7$ | OCH$_3$ | OCH$_3$ | |
| α-91 | C$_2$H$_5$ | C$_2$H$_5$ | CH$_3$ | OCH$_3$ | |
| α-92 | C$_2$H$_5$ | C$_2$H$_5$ | CH$_3$ | CH$_3$ | |
| α-93 | C$_2$H$_5$ | n-C$_3$H$_7$ | CH$_3$ | OCH$_3$ | |
| α-94 | C$_2$H$_5$ | n-C$_3$H$_7$ | CH$_3$ | CH$_3$ | |
| α-95 | iso-C$_3$H$_7$ | C$_2$H$_5$ | CH$_3$ | OCH$_3$ | |
| α-96 | iso-C$_3$H$_7$ | C$_2$H$_5$ | CH$_3$ | CH$_3$ | |
| α-97 | cyclopropyl | C$_2$H$_5$ | CH$_3$ | OCH$_3$ | |
| α-98 | cyclopropyl | C$_2$H$_5$ | CH$_3$ | CH$_3$ | |
| α-99 | sec-C$_4$H$_9$ | C$_2$H$_5$ | CH$_3$ | OCH$_3$ | |
| α-100 | sec-C$_4$H$_9$ | C$_2$H$_5$ | CH$_3$ | CH$_3$ | |
| α-101 | C$_2$H$_5$ | iso-C$_3$H$_7$ | CH$_3$ | OCH$_3$ | |
| α-102 | C$_2$H$_5$ | iso-C$_3$H$_7$ | CH$_3$ | CH$_3$ | |

TABLE 2-β

| Compound No. | $R_1$ | $R_2$ | X | Y | Physical Properties m.p. (°C.) |
|---|---|---|---|---|---|
| β-1 | iso-$C_3H_7$ | $C_2H_5$ | $CH_3$ | $OCH_3$ | 146–148 |
| β-2 | iso-$C_3H_7$ | $C_2H_5$ | $OCH_3$ | $OCH_3$ | 144–146 |
| β-3 | $C_2H_5$ | n-$C_3H_7$ | $CH_3$ | $OCH_3$ | 152–154 |
| β-4 | iso-$C_3H_7$ | n-$C_4H_9$ | $CH_3$ | $OCH_3$ | 162-164 |
| β-5 | iso-$C_3H_7$ | n-$C_3H_7$ | $OCH_3$ | $OCH_3$ | 136–139 |
| β-6 | $C_2H_5$ | iso-$C_3H_7$ | $CH_3$ | $OCH_3$ | 142–144 |
| β-7 | $C_2H_5$ | iso-$C_3H_7$ | $OCH_3$ | $OCH_3$ | 142–143 |
| β-8 | $C_2H_5$ | n-$C_3H_7$ | $OCH_3$ | $OCH_3$ | 151–154 |
| β-9 | $C_2H_5$ | $C_2H_5$ | $OCH_3$ | $OCH_3$ | |
| β-10 | $C_2H_5$ | n-$C_4H_9$ | $CH_3$ | $OCH_3$ | |
| β-11 | $C_2H_5$ | n-$C_4H_9$ | $OCH_3$ | $OCH_3$ | |
| β-12 | $C_2H_5$ | sec-$C_4H_9$ | $CH_3$ | $OCH_3$ | |
| β-13 | $C_2H_5$ | sec-$C_4H_9$ | $OCH_3$ | $OCH_3$ | |
| β-14 | n-$C_3H_7$ | $C_2H_5$ | $CH_3$ | $OCH_3$ | |
| β-15 | n-$C_3H_7$ | $C_2H_5$ | $OCH_3$ | $OCH_3$ | |
| β-16 | iso-$C_3H_7$ | n-$C_3H_7$ | $CH_3$ | $OCH_3$ | |
| β-17 | iso-$C_3H_7$ | iso-$C_3H_7$ | $CH_3$ | $OCH_3$ | |
| β-18 | iso-$C_3H_7$ | iso-$C_3H_7$ | $OCH_3$ | $OCH_3$ | |
| β-19 | iso-$C_3H_7$ | n-$C_4H_9$ | $OCH_3$ | $OCH_3$ | |
| β-20 | iso-$C_3H_7$ | sec-$C_4H_9$ | $CH_3$ | $OCH_3$ | |
| β-21 | iso-$C_3H_7$ | sec-$C_4H_9$ | $OCH_3$ | $OCH_3$ | |
| β-22 | n-$C_3H_7$ | n-$C_4H_9$ | $CH_3$ | $OCH_3$ | 159–161 |
| β-23 | n-$C_3H_7$ | n-$C_4H_9$ | $OCH_3$ | $OCH_3$ | |
| β-24 | n-$C_3H_7$ | sec-$C_4H_9$ | $CH_3$ | $OCH_3$ | |
| β-25 | n-$C_3H_7$ | sec-$C_4H_9$ | $OCH_3$ | $OCH_3$ | |
| β-26 | n-$C_3H_7$ | n-$C_3H_7$ | $OCH_3$ | $OCH_3$ | |
| β-27 | n-$C_3H_7$ | iso-$C_3H_7$ | $CH_3$ | $OCH_3$ | |
| β-28 | n-$C_3H_7$ | iso-$C_3H_7$ | $OCH_3$ | $OCH_3$ | |
| β-29 | sec-$C_4H_9$ | $C_2H_5$ | $CH_3$ | $OCH_3$ | |
| β-30 | sec-$C_4H_9$ | $C_2H_5$ | $OCH_3$ | $OCH_3$ | |
| β-31 | $CH_3$ | n-$C_3H_7$ | $CH_3$ | $OCH_3$ | 152–155 |
| β-32 | $CH_3$ | n-$C_4H_9$ | $CH_3$ | $OCH_3$ | 162–167 |
| β-33 | $CH_3$ | iso-$C_4H_9$ | $CH_3$ | $OCH_3$ | 145–148 |
| β-34 | $CH_3$ | sec-$C_4H_9$ | $CH_3$ | $OCH_3$ | 160–162 |
| β-35 | $CH_3$ | $CH_2OCH_3$ | $CH_3$ | $OCH_3$ | 155–159 |
| β-36 | $C_2H_5$ | $CH_3$ | $CH_3$ | $OCH_3$ | 145–148 |
| β-37 | $C_2H_5$ | $C_2H_5$ | $CH_3$ | $OCH_3$ | 154–157 |
| β-38 | $C_2H_5$ | $CH_2OCH_3$ | $CH_3$ | $OCH_3$ | 153–158 |
| β-39 | n-$C_3H_7$ | $CH_3$ | $CH_3$ | $OCH_3$ | 152–154 |
| β-40 | n-$C_3H_7$ | n-$C_3H_7$ | $CH_3$ | $OCH_3$ | |
| β-41 | iso-$C_3H_7$ | $OCH_3$ | $CH_3$ | $OCH_3$ | 141–143 |
| β-42 | n-$C_4H_9$ | n-$C_3H_7$ | $CH_3$ | $OCH_3$ | 158–160 |
| β-43 | n-$C_4H_9$ | n-$C_4H_9$ | $CH_3$ | $OCH_3$ | 157–159 |
| β-44 | $CH_3$ | $OCH_3$ | $CH_3$ | $OCH_3$ | |
| β-45 | $C_2H_5$ | $OCH_3$ | $CH_3$ | $OCH_3$ | |
| β-46 | iso-$C_3H_7$ | $OCH_3$ | $OCH_3$ | $OCH_3$ | |
| β-47 | n-$C_4H_9$ | $OCH_3$ | $CH_3$ | $OCH_3$ | |
| β-48 | $CH_3$ | $OC_2H_5$ | $CH_3$ | $OCH_3$ | |
| β-49 | n-$C_3H_7$ | $OC_2H_5$ | $CH_3$ | $OCH_3$ | |
| β-50 | $CF_3$ | $OCH_3$ | $CH_3$ | $OCH_3$ | |
| β-51 | $CF_3$ | $OC_2H_5$ | $CH_3$ | $OCH_3$ | |
| β-52 | $CH_2CF_3$ | $OCH_3$ | $CH_3$ | $OCH_3$ | |
| β-53 | $CH_2CF_3$ | $CH_2OCH_3$ | $CH_3$ | $OCH_3$ | 137-144 |
| β-54 | $CH_3CH(Cl)$ | $C_2H_5$ | $CH_3$ | $OCH_3$ | 155–157 |
| β-55 | $CH_3CH(Cl)$ | $C_2H_5$ | $OCH_3$ | $OCH_3$ | 139–141 |
| β-56 | $CHCl_2$ | $C_2H_5$ | $CH_3$ | $OCH_3$ | 155–157 |
| β-57 | $CHCl_2$ | $C_2H_5$ | $OCH_3$ | $OCH_3$ | 157–159 |
| β-58 | $CH_3CH(F)$ | $C_2H_5$ | $CH_3$ | $OCH_3$ | 136–141 |
| β-59 | $CH_3CH(F)$ | $C_2H_5$ | $OCH_3$ | $OCH_3$ | |
| β-60 | $CH_2Cl$ | $C_2H_5$ | $CH_3$ | $OCH_3$ | 172–174 |
| β-61 | $CH_2Cl$ | $C_2H_5$ | $OCH_3$ | $OCH_3$ | |
| β-62 | $CH_3CH(CF_3)$ | $C_2H_5$ | $CH_3$ | $OCH_3$ | |
| β-63 | $CH_3CH(CF_3)$ | $C_2H_5$ | $OCH_3$ | $OCH_3$ | |
| β-64 | $CH_3CH(CHF_2)$ | $C_2H_5$ | $CH_3$ | $OCH_3$ | |
| β-65 | $CH_3CH(CHF_2)$ | $C_2H_5$ | $OCH_3$ | $OCH_3$ | |
| β-66 | $CH_3CH(CH_2F)$ | $C_2H_5$ | $CH_3$ | $OCH_3$ | |
| β-67 | $CH_3CH(CH_2F)$ | $C_2H_5$ | $OCH_3$ | $OCH_3$ | |
| β-68 | $CH_2Cl$ | $CH_3$ | $CH_3$ | $OCH_3$ | |
| β-69 | $CH_2Cl$ | $CH_3$ | $OCH_3$ | $OCH_3$ | |
| β-70 | $CH_2Cl$ | n-$C_3H_7$ | $CH_3$ | $OCH_3$ | |
| β-71 | $CH_2Cl$ | n-$C_3H_7$ | $OCH_3$ | $OCH_3$ | |
| β-72 | $CHF_2$ | $C_2H_5$ | $CH_3$ | $OCH_3$ | |
| β-73 | $CH_2F$ | $C_2H_5$ | $CH_3$ | $OCH_3$ | |
| β-74 | $CH_3CF_2$ | $C_2H_5$ | $CH_3$ | $OCH_3$ | |

TABLE 2-β-continued

| Compound No. | $R_1$ | $R_2$ | X | Y | Physical Properties m.p. (°C.) |
|---|---|---|---|---|---|
| β-75 | $CH_3CH(Cl)$ | $CH_2CF_3$ | $CH_3$ | $OCH_3$ | |
| β-76 | $CH_3CH(Cl)$ | $CH_2CH_2F$ | $CH_3$ | $OCH_3$ | |
| β-77 | $CH_3CH(Cl)$ | $CH_3CH_2Cl$ | $CH_3$ | $OCH_3$ | |
| β-78 | $CH_3CH(Br)$ | $C_2H_5$ | $CH_3$ | $OCH_3$ | 157–159 |
| β-79 | $CH_2CF_3$ | $C_2H_5$ | $CH_3$ | $OCH_3$ | 150–152 |
| β-80 | iso-$C_4H_9$ | sec-$C_4H_9$ | $CH_3$ | $OCH_3$ | 85–90 |
| β-81 | sec-$C_4H_9$ | sec-$C_4H_9$ | $CH_3$ | $OCH_3$ | 75–80 |
| β-82 | n-$C_4H_9$ | iso-$C_4H_9$ | $CH_3$ | $OCH_3$ | oily substance |
| β-83 | sec-$C_4H_9$ | iso-$C_4H_9$ | $CH_3$ | $OCH_3$ | |
| β-84 | n-$C_4H_9$ | sec-$C_4H_9$ | $CH_3$ | $OCH_3$ | 65–69 |
| β-85 | $CH_3CH(Cl)$ | $CH_3$ | $CH_3$ | $OCH_3$ | 161–163 |
| β-86 | $CH_3CH(Cl)$ | n-$C_3H_7$ | $CH_3$ | $OCH_3$ | 159–160 |
| β-87 | $(CH_3)2CCl$ | $C_2H_5$ | $CH_3$ | $OCH_3$ | 145–146 |
| β-88 | $CH_3CH_2CH(Cl)$ | $C_2H_5$ | $CH_3$ | $OCH_3$ | 148–150 |
| β-89 | $CBr_3$ | $CH_3$ | $CH_3$ | $OCH_3$ | 125–127 |
| β-90 | $CBr_3$ | $C_2H_5$ | $CH_3$ | $OCH_3$ | 109–111 (decomposition) |
| β-91 | $CCl_3$ | $C_2H_5$ | $CH_3$ | $OCH_3$ | 154–156 |
| β-92 | $CH_2CF_3$ | $C_2H_5$ | $OCH_3$ | $OCH_3$ | 163–165 |
| β-93 | $CH_3CH(Cl)$ | iso-$C_3H_7$ | $CH_3$ | $OCH_3$ | 148–151 |
| β-94 | $(CH_2)_2OC_2H_5$ | $C_2H_5$ | $CH_3$ | $OCH_3$ | 124–127 |
| β-95 | $CH_2CF_3$ | n-$C_3H_7$ | $CH_3$ | $OCH_3$ | 157–158 |
| β-96 | $CF_3$ | $CH_2OCH_3$ | $CH_3$ | $OCH_3$ | 130–132 |
| β-97 | $CH_3CH(Cl)$ | $CH_3$ | $CH_3$ | $CH_3$ | |
| β-98 | $CH_3CH(Cl)$ | $C_2H_5$ | $CH_3$ | $CH_3$ | |
| β-99 | $CH_3CH(Cl)$ | $C_2H_5$ | $CH_3$ | $OC_2H_5$ | |
| β-100 | $CH_3CH(Cl)$ | $C_2H_5$ | $C_2H_5$ | $OCH_3$ | |
| β-101 | $CH_3CH(OCH_3)$ | $CH_3$ | $CH_3$ | $OCH_3$ | |
| β-102 | $CH_3CH(OCH_3)$ | $CH_3$ | $OCH_3$ | $OCH_3$ | |
| β-103 | $CH_3CH(OCH_3)$ | $C_2H_5$ | $CH_3$ | $OCH_3$ | |
| β-104 | $CH_3CH(OCH_3)$ | $C_2H_5$ | $OCH_3$ | $OCH_3$ | |
| β-105 | $CH_3CH(OC_2H_5)$ | $CH_3$ | $CH_3$ | $OCH_3$ | |
| β-106 | $CH_3CH(OC_2H_5)$ | $CH_3$ | $OCH_3$ | $OCH_3$ | |
| β-107 | $CH_3CH(OC_2H_5)$ | $C_2H_5$ | $CH_3$ | $OCH_3$ | |
| β-108 | $CH_3CH(OC_2H_5)$ | $C_2H_5$ | $OCH_3$ | $OCH_3$ | |
| β-109 | iso-$C_3H_7$ | $C_2H_5$ | $CH_3$ | $CH_3$ | |
| β-110 | iso-$C_3H_7$ | $C_2H_5$ | $CH_3$ | $OC_2H_5$ | |
| β-111 | Na salt of Compound No. β-1 | | | | |
| β-112 | Na salt of Compound No. β-2 | | | | |
| β-113 | Na salt of Compound No. β-54 | | | | |
| β-114 | Monomethylamine salt of Compound No. β-54 | | | | |

In Table 1, the physical properties of Intermediate Nos. 45 to 48, 69, 71, 90, 92, 105, 106, 107, 109 to 112, 114, and 118 are of the respective racemic modification.

In Table 2-α, the physical properties of Compound Nos. α-46 and α-47 are of the respective racemic modification.

In Table 2-β, the physical properties of Compound Nos. β-34, β-54, β-55, β-58, β-78, β-80, β-81, β-83 to β-86, β-88, and β-93 are of the respective racemic modification.

As the effective ingredient of the herbicide, the substituted pyridinesulfonamide compound or its salt of the present invention, as will be evident from the test examples given hereinafter, exhibits a wide herbicidal spectrum at a low dosage while it shows safety on soybean, wheat, cotton, etc.

The herbicide of the present invention can be applied to a wide variety of sites including agricultural fields such as upland fields, orchards and mulberry fields, and non-agricultural fields such as forests, farm roads, playgrounds and factory sites. The method of application of the herbicide of the present invention can be arbitrarily chosen from a soil treatment application and a foliage treatment application. The herbicide of the present invention may be applied in the form of a formulation such as a dust, granules, water-dispersible granules, a wettable powder, an emulsifiable concentrate, a soluble concentrate, and a suspension concentrate, which is prepared by blending the substituted pyridinesulfonamide compound or its salt of the present invention as the effective ingredient usually with a carrier and, if necessary, further with various other adjuvants selected from among diluents, solvents, emulsifiers, spreaders, surfactants, etc. The suitable blending weight ratio of the effective ingredient to the agricultural adjuvants may be in the range of 1:99 to 90:10, preferably in the range of 5:95 to 80:20. The suitable amount of the effective ingredient to be used cannot be unequivocally determined because it varies depending on weather conditions, soil conditions, the form of the above-mentioned formulation, the kinds of object weeds, and the application season, However, the amount of the effective ingredient to be applied is generally in the range of 0,005 g to 50 g/a (are), preferably in the range of 0.01 to 10 g/a, more preferably in the range of 0.05 to 5 g/a.

The herbicide of the present invention may be used in mixture or combination with at least one ingredient or component selected from among other agricultural chemicals, agricultural adjuvants, phytotoxicity-reducing agents, etc. to sometimes exhibit improvements in effect and functions. The herbicide of the present invention may be used in mixture or combination with at least one other compound as an effective ingredient of herbicide, in which case a synergistic effect can sometimes be attained.

The other compound may be formulated together with the compound of the present invention, or its own preparation may be mixed with the herbicide of the present invention upon use.

Examples of the other compound are as follows:
Phenoxypropionate compounds such as
ethyl (±)-2-[4-[(6-chloro-2-quinoxalinyl)oxy]phenoxy]propionate (common name: quizalofop-ethyl)
ethyl (±)-2-[4-[(6-chloro-2-benzoxazolyl)oxy]phenoxy]propionate (common name: fenoxaprop-ethyl)
butyl (±)-2-[4-[[5-(trifluoromethyl)-2-pyridinyl]oxy]phenoxy]propionate (common name: fluazifop-butyl)
methyl 2-[4-[[3-chloro-5-(trifluoromethyl)-2-pyridinyl]oxy]phenoxy]propionate (common name: haloxyfopmethyl)
2-ethoxyethyl 2-[4-[[3-chloro-5-(trifluoromethyl)-2-pyridinyl]oxy]phenoxy]propionate (common name: haloxyfopetotyl)
(R)-2-[[(1-methylethylidene)amino]oxy]ethyl 2-[4-[6-chloro-2-quinoxalinyl)oxy]phenoxy] propanoate (common name: propaquizafop);
Diphenyl ether compounds such as
sodium 5-[2-chloro-4-(trifluoromethyl)phenoxy]-2-nitrobenzoate (common name: acifluorfen-sodium)
(±)-2-ethoxy-1-methyl-2-oxoethyl-5-[2-chloro-4-(trifluoromethyl)phenoxy]-2-nitrobenzoate (common name: lactofen)
5-[2-chloro-4-(trifluoromethyl)phenoxy]-N-(methylsulfonyl)-2-nitrobenzamide (common name: fomesafen);
Haloacetamide compounds such as
2-chloro-N-(2-ethyl-6-methylphenyl)-N-(2-methoxy-1-methylethyl)acetamide (common name: metolachlor)
2-chloro-N-(2,6-diethylphenyl)-N-(methoxymethyl)acetamide (common name: alachlor);
N-[2,4-dimethyl-5-[[(trifluoromethyl)sulfonyl)amino]phenyl]acetamide (common name: mefluidide)
Imidazolinone compounds such as
(±)-2-[4,5-dihydro-4-methyl-4-(1-methylethyl)-5-oxo-1H-imidazol-2-yl]- 5-ethyl-3-pyridinecarboxylic acid (common name: imazethapyr)
2-[4,5-dihydro-4-methyl-4-(1-methylethyl)-5-oxo-1H-imidazol-2-yl]- 3-quinolinecarboxylic acid (common name: imazaquin);
Dinitroaniline compounds such as
2,6-dinitro-N,N-dipropyl-4-(trifluoromethyl)aniline (common name: trifluralin)
N-(1-ethylpropyl)-3,4-dimethyl-2,6-dinitroaniline (common name: pendimethalin);
N-ethyl-α,α,α-trifluoro-N-(2-methylallyl)-2,6-dinitro-p-toluidine (common name: ethalfluralin)
Carbamate compounds such as
3-[(methoxycarbonyl)amino]phenyl (3-methylphenyl)carbamate (common name: phenmedipham)
ethyl [3-[[(phenylamino)carbonyl]oxy]phenyl]carbamate (common name: desmedipham);
S-ethyl dipropylcarbamothioate (common name: EPTC)
S-propyl dipropylthiocarbamate (common name: vernolate)
Cyclohexane dione compounds such as
2-[1-(ethoxyimino)butyl]-5-[2-(ethylthio)propyl]-3-hydroxy-2-cyclohexen-1-one (common name: sethoxydim);
Sulfonylurea compounds such as
ethyl 2-[[[[(4-chloro-6-methoxy-2-pyrimidinyl)amino]carbonyl]amino]sulfonyl]benzoate (common name: chlorimuron-ethyl)
methyl 3-[[[[(4-methoxy-6-methyl-1,3,5-triazin-2-yl)amino]carbonyl]amino]sulfonyl]- 2-thiophenecarboxylate (common name: thifensulfuron-methyl); and Compounds such as
3-(1-methylethyl)-(1H)-2,1,3-benzothiadiazin-4(3H)-one-2,2-dioxide (common name: bentazon)
4-(2,4-dichlorophenoxy)butanoic acid (common name: 2,4-DB)
3-(3,4-dichlorophenyl)-1-methoxy-1-methylurea (common name: linuron)
4-amino-6-(1,1-dimethylethyl)-3-(methylthio)-1,2,4-triazin-5(4H)-one (common name: metribuzin)
7-oxabicyclo[2.2.1]heptane-2,3-dicarboxylic acid (common name: endothal)
(±)-2-ethoxy-2,3-dihydro-3,3-dimethyl-5-benzofuranyl methanesulfonate (common name: ethofumesate)
5-amino-4-chloro-2-phenyl-3(2H)-pyridazinone (Common name: chloridazon)
4-chloro-5-methylamino-2-(α,α,α-trifluoro-m-tolyl)pyridazin-3(2H)-one (common name: norflurazon)
2-(2-chlorobenzyl)-4,4-dimethyl-1,2-oxazolidin-3-one (common name: clomazone)

The amount of at least one compound selected from the above-exemplified other compound, based on the amount of the substituted pyridinesulfonamide compound or its salt as the effective ingredient of the herbicide of the present invention to be mixed therewith, may be in a comparatively wide range. However, the amount of the above-exemplified other compound is usually 0.002 to 1000 parts by weight, per part by weight of the substituted pyridinesulfonamide compound or its salt of the present invention.

In particular, the phenoxypropionate compounds, the imidazolinone compounds and the cyclohexane dione compounds are usually 0.04 to 100 parts by weight, the haloacetamide compounds and the dinitroaniline compounds are usually 1 to 600 parts by weight, the sulfonylurea compounds are usually 0.002 to 10 parts by weight, and a compound other than the above other compound is usually 0.02 to 800 parts by weight, per part by weight of the substituted pyridinesulfonamide compound or its salt of the present invention.

The substituted pyridinesulfonamide compound or its salt as the effective ingredient of the herbicide of the present invention may be used in an amount of 0.05 to 5 g/a in combination with at least one compound selected from the above-exemplified other compound in an amount of 0.01 to 50 g/a.

In particular, the phenoxypropionate compounds, the imidazolinone compounds and the cyclohexane dione compounds may be used in an amount of 0.2 to 5 g/a, the haloacetamide compounds and the dinitroaniline compounds may be used in an amount of 5 to 30 g/a, the sulfonylurea compounds may be used in an amount of 0.01 to 0.5 g/a, and the compound other than the above other compound pound may be further used in an amount of 0.1 to 40 g/a in combination with the substituted pyridinesulfonamide compound or its salt of the present invention.

Further, the following other compound as an effective ingredient of herbicide may be also used in mixture or combination with the herbicide of the present invention, where a synergistic effect can be attained, too.

Sulfonylurea compounds such as
methyl 2-[[[[(4-methoxy-6-methyl-1,3,5-triazin-2-yl)amino]carbonyl]amino]sulfonyl]benzoate (common name: metsulfuron-methyl)
methyl 2-[[[[N-(4-methoxy-6-methyl-1,3,5-triazin-2-yl)methylamino]carbonyl]amino]sulfonyl] benzoate (common name: tribenuron-methyl)
2-chloro-N-[[(4-methoxy-6-methyl-1,3,5-triazin-2-yl]amino]carbonyl]benzenesulfonamide (common name: chlorsulfuron);

Phenoxypropionate compounds such as
methyl (±)-2-[4-(2,4-dichlorophenoxy)phenoxy]propionate (common name: diclofop-methyl);
Imidazolinone compounds such as
mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate (common name: imazamethabenz); and
Other compounds such as
1,2-dimethyl-3,5-diphenyl-1H-pyrazolium methylsulfate (common name: difenzoquat methylsulfate)
3,5-dibromo-4-hydroxybenzonitrile (common name: bromoxynil)
4-hydroxy-3,5-diiodobenzonitrile (common name: ioxynil)
2,4-dichlorophenoxyacetic acid (common name: 2,4-D)
S-(2,3,3-trichloro-2-propenyl)-bis(1-methylethyl)carbamothioate (common name: triallate)
4-chloro-2-methylphenoxyacetic acid (common name: MCPA)
3,6-dichloro-2-pyridinecarboxylic acid (common name: clopyralid)
O-(6-chloro-3-phenyl-4-pyridazinyl)-S-octyl thiocarbonothioate (common name: pyridate)
3,6-dichloro-2-methoxybenzoic acid (common name: dicamba)
N'-(3,4-dichlorophenyl)-N,N-dimethylurea (common name: diuron)
4-amino-3,5,6-trichloro-2-pyridinecarboxylic acid (common name: picloram)
N,N-dimethyl N'-[3-(trifluoromethyl)phenyl]urea (common name: fluometuron)
2-[[4-chloro-6-(ethylamino)-1,3,5-triazin-2-yl]amino]-2-methylpropionitrile (common name: cyanazine)
N,N'-bis(1-methylethyl)-6-(methylthio)-1,3,5-triazine-2,4-diamine (common name: prometryn)
N-(3,4-dichlorophenyl)propanamide (common name: propanil)
disodium salt of methylarsonic acid (common name: DSMA)
monosodium salt of methylarsonic acid (common name: MSMA)
2-chloro-1-(3-ethoxy-4-nitrophenoxy)-4-(trifluoromethyl)benzene (common name: oxyfluorfen)
O,O-bis(1-methylethyl) S-[2-[(phenylsulfonyl)amino]ethyl] phosphorodithioate (common name: bensulide.)
2-(3,4-dichlorophenyl)-4-methyl-1,2,4-oxadiazolidine3,5-dione (common name: methazole)
4-chloro-5-(methylamino)-2-[3-(trifluoromethyl)phenyl]-3(2H)-pyridazinone (common name: norflurazon)
2-chloro-6-(4,6-dimethoxypyrimidin-2-ylthio)benzoate (common name: pyrithiobac)
ethyl 2-chloro-6-(4,6-dimethoxypyrimidin-2-ylthio)benzoate (common name: pyrithiobac-ethyl)
sodium 2-chloro-6-(4,6-dimethoxypyrimidin-2-ylthio)benzoate (common name: pyrithiobac-sodium)

The amount of at least one compound selected from the above-exemplified other compound, based on the amount of the substituted pyridinesulfonamide compound or its salt as the effective ingredient of the herbicide of the present invention to be mixed therewith, may be in a comparatively wide range. However, the amount of the above-exemplified other compound is usually 0.002 to 1000 parts by weight, per part by weight of the substituted pyridinesulfonamide compound or its salt of the present invention.

The substituted pyridinesulfonamide compound or its salt as the effective ingredient of the herbicide of the present invention may be used in an amount of 0.05 to 5 g/a in combination with at least one compound selected from the above-exemplified other compound in an amount of 0.01 to 50 g/a.

Test Examples, using the herbicide of the present invention, will now be described.

TEST EXAMPLE 1

1/1,500 are [are (a)=100 m$^2$] pots were filled with upland soil, which in the pots was then sown with a variety of plant seeds. The plants grown will be enumerated below.

| Name | Abbreviation |
|---|---|
| rice (*Oryza sativa*) | OR |
| soybean (*Glycine max*) | GL |
| corn (*Zea mays*) | ZE |
| cotton (*Gossypium*) | GO |
| wheat (*Triticum*) | TR |
| cocklebur (*Xanthium strumarium*) | XA |
| morning glory (*Ipomoea purpurea*) | IP |
| prickly sida (*Sida spinosa*) | SI |
| slender amaranth (*Amaranthus viridis*) | AM |
| barnyard grass (*Echinochloa crus-galli*) | EC |
| large crabgrass (*Digitaria adscendens*) | DI |

When each plant reached a given growth stage (a 1.3- to 3.0-leaf stage for rice, primary leaf to a 1.2-leaf stage for soybean, 2.3- to 4.1-leaf stage for corn, cotyledon to 1.1-leaf stage for cotton, 2.2- to 3.0-leaf stage for wheat, 1.0- to 3.2-leaf stage for cocklebur, 0.3- to 2.0-leaf stage for morning glory, 0.1- to 1.8-leaf stage for prickly sida, 0.3- to 2.4-leaf stage for slender amaranth, 1.7- to 3.3-leaf stage for barnyard glass, and 1.4- to 3.1-leaf stage for large crabgrass), a predetermined amount of the herbicide of the present invention in the form of a wettable powder, weighed out, diluted with 5 l/a of water and admixed with 0.2 vol %, based on the resulting composition, of an agricultural spreader, was foliarly applied to the plant with a small Spray gun. The progress of growth of the plant was visually observed 17 to 29 days after the foliar application to evaluate the degree of growth control according to 10 ratings (1: the same as in an untreated plot–10: perfect growth control). The results are listed in Table 3.

TABLE 3

| Compound No. | Amount of Effective Ingredient (g/a) | OR | GL | ZE | GO | TR | XA | IP | SI | AM | EC | DI | Day* |
|---|---|---|---|---|---|---|---|---|---|---|---|---|---|
| α-1 | 1.25 | 8 | 7 | 10 | 8 | | 9 | 7 | 7 | 7 | 5 | | 18 |
| α-2 | 1.25 | 8 | 3 | 10 | | 5 | 10 | 8 | 5 | 6 | 9 | 9 | 29 |
|  | 0.31 | 7 | 2 | 9 | | 1 | 6 | 5 | 3 | 3 | 7 | 2 | |
| α-3 | 1.25 | 7 | 3 | 10 | | 8 | 9 | 7 | 6 | 9 | 9 | 8 | 22 |

TABLE 3-continued

| Compound No. | Amount of Effective Ingredient (g/a) | OR | GL | ZE | GO | TR | XA | IP | SI | AM | EC | DI | Day* |
|---|---|---|---|---|---|---|---|---|---|---|---|---|---|
|  | 0.31 | 5 | 3 | 8 |  | 5 | 4 | 5 | 5 | 8 | 10 | 7 |  |
| α-4 | 0.31 | 8 | 4 | 9 |  | 4 | 8 | 8 | 8 | 9 | 8 | 10 | 22 |
| α-5 | 1.25 | 8 | 10 | 10 | 9 |  | 10 | 9 | 6 | 10 | 7 |  | 24 |
|  | 0.31 | 8 | 10 | 10 | 8 |  | 10 | 9 | 6 | 9 | 5 |  |  |
| α-6 | 1.25 | 9 | 9 | 9 | 9 |  | 10 | 9 | 8 | 10 | 9 |  | 20 |
|  | 0.31 | 7 | 10 | 8 | 9 |  | 10 | 9 | 7 | 10 | 7 |  |  |
| α-7 | 1.25 | 7 | 9 | 9 | 9 |  | 10 | 10 | 8 | 10 | 7 |  | 20 |
|  | 0.31 | 6 | 9 | 8 | 8 |  | 10 | 7 | 6 | 9 | 7 |  |  |
| α-8 | 1.25 | 6 | 7 | 9 | 7 |  | 10 | 10 | 5 | 9 | 7 |  | 20 |
|  | 0.31 | 6 | 5 | 8 | 5 |  | 10 | 3 | 4 | 7 |  |  |  |
| α-11 | 1.25 | 8 | 7 | 10 |  |  | 10 | 10 | 6 | 10 | 10 | 3 | 21 |
|  | 0.31 | 7 | 6 | 10 |  |  | 10 | 10 | 5 | 10 | 10 | 3 |  |
| α-18 | 1.25 | 9 | 3 | 10 |  | 5 | 9 | 9 | 5 |  | 9 | 10 | 29 |
|  | 0.31 | 7 | 2 | 10 |  | 4 | 9 | 7 | 3 | 7 | 7 | 9 |  |
| α-19 | 1.25 | 6 | 5 | 10 |  | 4 | 10 | 7 | 6 | 9 | 10 | 9 | 23 |
|  | 0.31 | 5 | 5 | 10 |  | 2 | 9 | 6 | 3 | 5 | 9 | 9 |  |
| α-20 | 1.25 | 7 | 4 | 7 |  | 2 | 9 | 8 | 5 | 5 | 1 | 5 | 21 |
|  | 0.31 | 7 | 1 | 7 |  | 1 | 8 | 7 | 3 | 3 | 1 | 1 |  |
| α-21 | 1.25 | 6 | 7 | 10 |  | 2 | 10 | 7 | 3 | 7 | 6 | 4 | 23 |
|  | 0.31 | 5 | 7 | 9 |  | 1 | 9 | 6 | 2 | 6 | 4 | 3 |  |
| α-22 | 1.25 | 6 | 3 | 10 |  | 6 | 10 | 9 | 8 | 10 | 8 | 5 | 20 |
|  | 0.31 | 6 | 2 | 10 |  | 5 | 10 | 8 | 6 | 10 | 8 | 3 |  |
| α-23 | 1.25 | 1 | 4 | 3 |  | 2 | 7 | 5 | 6 | 9 | 2 | 2 | 20 |
| α-26 | 1.25 | 2 | 3 | 3 |  | 3 | 5 | 6 | 7 | 6 | 3 | 3 | 20 |
|  | 0.31 | 2 | 2 | 1 |  | 3 | 4 | 5 | 5 | 5 | 2 | 2 |  |
| α-27 | 1.25 | 2 | 1 | 3 |  | 3 | 9 | 3 | 4 | 7 | 4 | 3 | 20 |
|  | 0.31 | 1 | 1 | 2 |  | 3 | 8 | 1 | 2 | 6 | 3 | 3 |  |
| α-31 | 1.25 | 7 | 7 | 10 |  | 4 | 9 | 10 | 6 | 9 | 5 | 3 | 18 |
|  | 0.31 | 6 | 7 | 9 |  | 2 | 9 | 9 | 3 | 9 | 3 | 2 |  |
| α-32 | 1.25 | 3 | 6 | 4 |  | 4 | 9 | 9 | 7 | 10 | 3 | 3 | 18 |
|  | 0.31 | 1 | 6 | 4 |  | 3 | 9 | 9 | 6 | 10 | 1 | 3 |  |
| α-34 | 1.25 | 8 | 6 | 10 | 9 |  | 7 | 9 | 7 | 9 | 10 | 4 | 24 |
|  | 0.31 | 6 | 5 | 10 | 4 |  | 6 | 7 | 6 | 9 | 9 | 4 |  |
| α-37 | 1.25 | 8 | 9 | 10 | 6 |  | 10 | 7 | 10 | 10 | 10 | 6 | 21 |
|  | 0.31 | 7 | 9 | 10 | 5 |  | 10 | 6 | 10 | 10 | 10 | 5 |  |
| α-38 | 1.25 | 1 | 4 | 3 |  | 3 | 10 | 8 | 3 | 5 | 1 | 2 | 18 |
|  | 0.31 | 1 | 3 | 1 |  | 2 | 8 | 7 | 1 | 5 | 1 | 2 |  |
| α-39 | 1.25 | 1 | 6 | 1 |  | 1 | 9 | 4 | 6 | 9 | 4 | 1 | 20 |
|  | 0.31 | 1 | 3 | 1 |  | 1 | 9 | 3 | 5 | 8 | 2 | 1 |  |
| α-40 | 1.25 | 5 | 4 | 1 |  | 3 | 10 | 10 | 5 | 10 | 1 | 5 | 22 |
|  | 0.31 | 4 | 1 | 1 |  | 2 | 7 | 7 | 2 | 7 | 1 | 4 |  |
| α-41 | 1.25 | 1 | 3 | 1 |  | 2 | 9 | 6 | 6 | 8 | 1 | 2 | 20 |
|  | 0.31 | 1 | 2 | 1 |  | 1 | 6 | 4 | 4 | 6 | 1 | 1 |  |
| α-42 | 1.25 | 7 | 10 | 10 |  | 7 | 10 | 9 | 6 | 10 | 1 | 2 | 22 |
|  | 0.31 | 6 | 10 | 6 |  | 4 | 10 | 9 | 4 | 10 | 1 | 2 |  |
| α-43 | 1.25 | 4 | 9 | 6 |  | 3 | 10 | 9 | 7 | 10 | 4 | 4 | 22 |
|  | 0.31 | 4 | 9 | 4 |  | 2 | 9 | 6 | 6 | 10 | 4 | 2 |  |
| α-45 | 1.25 | 3 | 3 | 3 |  | 3 | 8 | 7 | 3 | 7 | 3 | 3 | 23 |
| α-46 | 1.25 | 5 | 5 | 10 | 3 |  | 10 | 10 | 6 | 10 | 10 | 3 | 26 |
|  | 0.31 | 4 | 4 | 10 | 2 |  | 9 | 8 | 4 | 10 | 10 | 1 |  |
| α-47 | 1.25 | 5 | 8 | 10 | 4 |  | 9 | 7 | 6 | 9 | 9 | 5 | 17 |
|  | 0.31 | 5 | 6 | 10 | 3 |  | 9 | 6 | 5 | 9 | 8 | 4 |  |
| α-50 | 1.25 | 7 | 4 | 10 | 6 |  | 10 | 10 | 6 | 10 | 10 | 4 | 21 |
|  | 0.31 | 6 | 3 | 10 | 5 |  | 10 | 10 | 5 | 10 | 10 | 3 |  |
| α-52 | 1.25 | 5 | 1 | 3 | 4 |  | 7 | 6 | 6 | 9 | 4 | 6 | 21 |
|  | 0.31 | 4 | 1 | 1 | 3 |  | 6 | 3 | 5 | 7 | 3 | 5 |  |
| α-53 | 1.25 | 2 | 4 | 4 | 3 |  | 10 | 4 | 3 | 6 | 4 | 2 | 26 |
| α-55 | 1.25 | 4 | 3 | 3 | 4 |  | 7 | 3 | 4 | 7 | 3 | 4 | 17 |
| α-56 | 1.25 | 6 | 7 | 9 | 6 |  | 10 | 4 | 6 | 9 | 6 | 6 | 17 |
|  | 0.31 | 5 | 7 | 10 | 6 |  | 9 | 3 | 5 | 7 | 5 | 6 |  |
| α-57 | 1.25 | 5 | 8 | 10 | 5 |  | 7 | 6 | 4 | 9 | 8 | 3 | 21 |
|  | 0.31 | 4 | 6 | 10 | 4 |  | 7 | 5 | 4 | 8 | 7 | 2 |  |
| α-58 | 1.25 | 7 | 6 | 4 |  | 6 | 6 | 6 | 2 | 6 | 3 | 6 | 22 |

*observation day after foliar application

TEST EXAMPLE 2

1/10,000 are (a) pots were filled with upland soil, which in the pots was then sown with a variety of plant seeds. The plants grown will be enumerated below.

| Name | Abbreviation |
| --- | --- |
| soybean (*Glycine max*) | GL |
| indian mallow (*Abutilon avicennae*) | AB |
| oriental senna (*Cassia obtusifolia*) | CA |

When each plant reached a given growth stage (a 0.1-leaf stage for soybean, a 1.1-leaf stage for indian mallow, and 0.1-leaf stage for oriental senna), a predetermined amount of the herbicide of the present invention in the form of a wettable powder, weighed out, diluted with 5 l/a of water and admixed with 0.2 vol %, based on the resulting composition, of an agricultural spreader, was foliarly applied to the plant with a small spray gun. The progress of growth of the plant was visually observed 28 days after the foliar application to evaluate the degree of growth control according to the same 10 ratings as in Test Example 1. The results are listed in Table 4.

TABLE 4

| Compound No. | Amount of Effective Ingredient (g/a) | GL | AB | CA |
| --- | --- | --- | --- | --- |
| α-2 | 5 | 4 | 10 | 9–10 |
|  | 1.25 | 3 | 9 | 8 |

TEST EXAMPLE 3

1/3,000 are (a) pot and 1/10,000 are (a) pots were filled with upland soil, which in the pots was then sown with a variety of plant seeds. The plants grown will be enumerated below.

| pot | Name | Abbreviation |
| --- | --- | --- |
| 1/3,000 a | soybean (*Glycine max*) | GL |
| 1/10,000 a | cocklebur (*Xanthium strumarium*) | XA |
| 1/10,000 a | morning glory (*Ipomoea purpurea*) | IP |
| 1/10,000 a | slender amaranth (*Amaranthus viridis*) | AM |
| 1/10,000 a | indian mallow (*Abutilon avicennae*) | AB |
| 1/10,000 a | oriental senna (*Cassia obtusifolia*) | CA |

When each plant reached a given growth stage (a 0.5-leaf stage soybean, a 1.0-leaf stage for cocklebur, a 1.1-leaf stage for morning glory, a 1.4-leaf stage for slender amaranth, a 1.2-leaf stage for indian mallow, and a 0.2-leaf stage for oriental senna), a predetermined amount of the herbicide of the present invention in the form of a wettable powder, weighed out, diluted with 5 l/a of water and admixed with 0.2 vol %, based on the resulting composition, of an agricultural Spreader, was foliarly applied to the plant with a small spray gun. Visual observations on the soybean and the other plants were made on 18 days and 24 days, respectively after the foliar application to evaluate the degree of growth control according to the same 10 ratings as in Test Example 1. The results are listed in Table 5.

TABLE 5

| Compound No. | Amount of Effective Ingredient (g/a) | GL | XA | IP | AM | AB | CA |
| --- | --- | --- | --- | --- | --- | --- | --- |
| α-18 | 1.25 | 2 | 9 | 8 | 6 | 9 | 6 |

TEST EXAMPLE 4

1/3,000 are (a) pot and 1/10,000 are (a) pots were filled with upland soil, which in the pots was then sown with a variety of plant seeds. The plants grown will be enumerated below.

| pot | Name | Abbreviation |
| --- | --- | --- |
| 1/3,000 a | soybean (*Glycine max*) | GL |
| 1/10,000 a | cocklebur (*Xanthium strumarium*) | XA |
| 1/10,000 a | morning glory (*Ipomoea purpurea*) | IP |
| 1/10,000 a | slender amaranth (*Amaranthus viridis*) | AM |
| 1/10,000 a | indian mallow (*Abutilon avicennae*) | AB |
| 1/10,000 a | oriental senna (*Cassia obtusifolia*) | CA |

When each plant reached a given growth stage (a primary-leaf stage for soybean, a 2.0-leaf stage for cocklebur, a 1.2-leaf stage for morning glory, a 1.2-leaf stage for slender amaranth, a 1.3-leaf stage for indian mallow, and a 0.2-leaf stage for oriental senna), a predetermined amount of the herbicide of the present invention in the form of a wettable powder, weighed out diluted with 5 l/a of water and admixed with 0.2 vol %, based on the resulting composition, of an agricultural spreader, was foliarly applied to the plant with a small spray gun. Visual observations on the soybean and the other plants were made on 20 days and 25 days, respectively after the foliar application to evaluate the degree of growth control according to the same 10 ratings as in Test Example 1. The results are listed in Table 6.

TABLE 6

| Compound No. | Amount of Effective Ingredient (g/a) | GL | XA | IP | AM | AB | CA |
| --- | --- | --- | --- | --- | --- | --- | --- |
| α-22 | 1.25 | 3 | 9–10 | 9–10 | 7 | 10 | 6–7 |

TEST EXAMPLE 5

1/10,000 are (a) pots were filled with upland soil, which in the pots was then sown with a variety of plant seeds. The plants grown will be enumerated below.

| Name | Abbreviation |
| --- | --- |
| wheat (*Triticum*) | TR |
| wild oat (*Avena fatua*) | AV |

When each plant reached a given growth stage (a 2.1-leaf stage for wheat and a 1.0-leaf stage for wild oat), a predetermined amount of the herbicide of the present invention in the form of a wettable powder, weighed out, diluted with 5 l/a of water and admixed with 0.2 vol %, based on the resulting composition, of an agricultural spreader, was foliarly applied to the plant with a small spray gun. The progress of growth of the plant was visually observed 19 days after the foliar application to evaluate the degree of growth control according to the same 10 ratings as in Test Example 1. The results are listed in Table 7.

TABLE 7

| Compound No. | Amount of Effective Ingredient (g/a) | TR | AV |
|---|---|---|---|
| α-47 | 1.25 | 3 | 8–9 |
| | 0.31 | 2–3 | 8 |
| | 0.08 | 2 | 7 |

TEST EXAMPLE 6

1/10,000 are (a) pots were filled with upland soil, which in the pots was then sown with a variety of plant seeds. The plants grown will be enumerated below.

| Name | Abbreviation |
|---|---|
| cotton (*Gossypium*) | GO |
| oriental senna (*Cassia obtusifolia*) | CA |
| large crabgrass (*Digitaria adscendens*) | DI |

When each plant reached a given growth stage (a cotyledon stage for cotton, a 0.2-leaf stage for oriental senna, and a 2.9-leaf stage for large crabgrass), a predetermined amount of the herbicide of the present invention in the form of a wettable powder, weighed out, diluted with 5 l/a of water and admixed with 0.2 vol %, based on the resulting composition, of an agricultural spreader, was foliarly applied to the plant with a small spray gun. The progress of growth of the plant was visually observed 28 days after the foliar application to evaluate the degree of growth control according to the same 10 ratings as in Test Example 1. The results are listed in Table 8.

TABLE 8

| Compound No. | Amount of Effective Ingredient (g/a) | GO | CA | DI |
|---|---|---|---|---|
| α-19 | 1.25 | 3 | 8–9 | 8–9 |
| | 0.31 | 2 | 7–8 | 7–8 |
| | 0.08 | 1 | 6 | 6–7 |

TEST EXAMPLE 7

1/1,500 are [are (a)=100 m$^2$] pots were filled with upland farming soil, which in the pots was then sown with a variety of plants. The plants grown will be enumerated below.

| Name | Abbreviation |
|---|---|
| rice (*Oryza sativa*) | OR |
| soybean (*Glycine max*) | GL |
| corn (*Zea mays*) | ZE |
| cotton (*Gossypium*) | GO |
| Wheat (*Triticum*) | TR |
| cocklebur (*Xanthium strumarium*) | XA |
| morning glory (*Ipomoea purpurea*) | IP |
| prickly sida (*Sida spinosa*) | SI |
| slender amaranth (*Amaranthus viridis*) | AM |
| barnyard grass (*Echinochloa crus-galli*) | EC |
| large crabgrass (*Digitaria adscendens*) | DI |

When each plant reached a given growth stage (a 1.2- to 3.0-leaf stage for rice, primary leaf to a 0.7-leaf stage for soybean, 2.1- to 3.6-leaf stage for corn, cotyledon to 0.7-leaf stage for cotton, 2.0- to 3.0-leaf stage for wheat, 0.3- to 3.4-leaf stage for cocklebur, 0.3- to 1.6-leaf stage for morning glory, 0.1- to 1.3-leaf stage for prickly sida, 0.1- to 1.3-leaf stage for slender amaranth, 1.5- to 3.2-leaf stage for barnyard glass, and 1.2- to 3.0-leaf stage for large crabgrass), a predetermined amount of the herbicide of the present invention in the form of a wettable powder, weighed out, diluted with 5 l/a of water and admixed with 0.2 or 0.1 vol %, based on the resulting composition, of an agricultural spreader, was foliarly applied to the plant with a small spray gun. The progress of growth of the plant was visually observed 20 to 31 days after the foliar application to evaluate the degree of growth control according to the same 10 ratings as in Test Example 1. The results are listed in Table 9.

TABLE 9

| Compound No. | Amount of Active Ingredient (g/a) | OR | GL | ZE | GO | TR | XA | IP | SI | AM | EC | DI | Day* |
|---|---|---|---|---|---|---|---|---|---|---|---|---|---|
| β-1 | 1.25 | 10 | 4 | 10 | | 8 | 10 | 9 | 9 | 10 | 10 | 8 | 26 |
| | 0.31 | 9 | 3 | 9 | | 8 | 9 | 8 | 8 | 10 | 9 | 8 | |
| β-2 | 1.25 | 10 | 3 | 10 | | 10 | 10 | 10 | 6 | 10 | 9 | 9 | 21 |
| | 0.31 | 8 | 2 | 9 | | 8 | 10 | 9 | 5 | 10 | 8 | 8 | |
| β-3 | 1.25 | 6 | 3 | 8 | | 4 | 8 | 5 | 6 | 10 | 9 | 6 | 27 |
| β-4 | 1.25 | 8 | 4 | 10 | | 2 | 9 | 6 | 6 | 9 | 7 | 3 | 31 |
| β-5 | 1.25 | 10 | 4 | 10 | | 10 | 10 | 9 | 5 | 10 | 10 | 6 | 21 |
| | 0.31 | 9 | 3 | 7 | | 9 | 10 | 8 | 4 | 9 | 10 | 5 | |
| β-6 | 1.25 | 6 | 3 | 10 | | 3 | 7 | 8 | 6 | 9 | 6 | 4 | 22 |
| β-7 | 1.25 | 3 | 3 | 10 | | 2 | 7 | 6 | 3 | 9 | 2 | 2 | 22 |
| β-8 | 1.25 | 3 | 4 | 5 | | 3 | 6 | 4 | 3 | 7 | 5 | 5 | 23 |

TABLE 9-continued

| Compound No. | Amount of Active Ingredient (g/a) | OR | GL | ZE | GO | TR | XA | IP | SI | AM | EC | DI | Day* |
|---|---|---|---|---|---|---|---|---|---|---|---|---|---|
| β-32 | 1.25 | 3 | 3 | 3 | | 2 | 6 | 5 | 4 | 6 | 3 | 6 | 27 |
| β-33 | 1.25 | 6 | 3 | 2 | | 3 | 3 | 4 | 3 | 6 | 3 | 6 | 32 |
| β-37 | 1.25 | 2 | 2 | 3 | | 1 | 4 | 3 | 3 | 9 | 4 | 2 | 31 |
| β-39 | 1.25 | 3 | 4 | 3 | | 3 | 5 | 5 | 3 | 9 | 3 | 4 | 21 |
| β-41 | 1.25 | 10 | 2 | 10 | 3 | | 8 | 6 | 5 | 9 | 10 | 9 | 20 |
|  | 0.31 | 9 | 1 | 10 | 1 | | 6 | 5 | 2 | 7 | 10 | 7 | |
| β-42 | 1.25 | 6 | 4 | 3 | | 4 | 6 | 4 | 3 | 10 | 3 | 5 | 21 |
| β-43 | 1.25 | 2 | 4 | 3 | | 3 | 6 | 3 | 3 | 5 | 3 | 6 | 21 |
| β-54 | 1.25 | 9 | 2 | 10 | 6 | | 10 | 9 | 7 | 9 | 10 | 3 | 21 |
|  | 0.31 | 9 | 1 | 10 | 4 | | 9 | 9 | 6 | 9 | 10 | 3 | |
| β-55 | 1.25 | 9 | 3 | 10 | 7 | | 10 | 9 | 6 | 6 | 10 | 7 | 23 |
|  | 0.31 | 9 | 2 | 10 | 5 | | 10 | 8 | 6 | 6 | 10 | 5 | |
| β-56 | 1.25 | 9 | 4 | 10 | | 10 | 10 | 10 | 8 | 10 | 10 | 10 | 24 |
|  | 0.31 | 9 | 3 | 10 | | 10 | 10 | 9 | 6 | 9 | 10 | 10 | |
| β-57 | 1.25 | 8 | 2 | 9 | 6 | | 10 | 10 | 8 | 9 | 8 | 9 | 25 |
|  | 0.31 | 6 | 1 | 6 | 6 | | 10 | 10 | 7 | 8 | 7 | 9 | |
| β-58 | 1.25 | 5 | 1 | 4 | 2 | | 8 | 6 | 7 | 8 | 6 | 7 | 21 |
|  | 0.31 | 4 | 1 | 3 | 2 | | 7 | 5 | 6 | 7 | 5 | 7 | |
| β-60 | 1.25 | 6 | 4 | 5 | | 2 | 9 | 7 | 5 | 9 | 6 | 4 | 21 |
| β-78 | 1.25 | 10 | 10 | 10 | 9 | | 10 | 10 | 6 | 4 | 10 | 8 | 20 |
|  | 0.31 | 9 | 6 | 10 | 8 | | 10 | 10 | 5 | 3 | 10 | 6 | |
| β-79 | 1.25 | 1 | 6 | 1 | 6 | | 6 | 7 | 3 | 6 | 1 | 3 | 31 |
| β-80 | 1.25 | 3 | 6 | 2 | | 4 | 6 | 5 | 3 | 7 | 4 | 2 | 21 |
|  | 0.31 | 1 | 5 | 1 | | 3 | 6 | 5 | 3 | 6 | 3 | 2 | |
| β-81 | 1.25 | 5 | 6 | 2 | | 2 | 9 | 6 | 2 | 3 | 6 | 3 | 21 |
| β-82 | 1.25 | 4 | 3 | 8 | | 4 | 9 | 6 | 1 | 7 | 4 | 3 | 22 |
| β-84 | 1.25 | 6 | 6 | 3 | | 6 | 7 | 6 | 3 | 8 | 5 | 4 | 21 |
|  | 0.31 | 5 | 5 | 2 | | 5 | 6 | 6 | 2 | 7 | 5 | 3 | |
| β-85 | 1.25 | 10 | 5 | 10 | 6 | | 10 | 10 | 6 | 7 | 10 | 6 | 20 |
|  | 0.31 | 9 | 2 | 10 | 3 | | 9 | 7 | 4 | 5 | 10 | 5 | |
| β-86 | 1.25 | 10 | 10 | 10 | 9 | | 10 | 10 | 5 | 6 | 10 | 6 | 20 |
|  | 0.31 | 9 | 6 | 10 | 8 | | 9 | 10 | 4 | 5 | 10 | 3 | |
| β-87 | 1.25 | 8 | 6 | 9 | 6 | | 10 | 10 | 4 | 6 | 5 | 3 | 20 |
|  | 0.31 | 6 | 3 | 8 | 3 | | 10 | 6 | 2 | 4 | 3 | 2 | |
| β-88 | 1.25 | 10 | 6 | 10 | 6 | | 10 | 10 | 6 | 6 | 10 | 6 | 22 |
|  | 0.31 | 9 | 5 | 10 | 6 | | 10 | 10 | 5 | 5 | 10 | 5 | |
| β-89 | 1.25 | 9 | 9 | 9 | 5 | | 10 | 10 | 5 | 7 | 10 | 7 | 21 |
|  | 0.31 | 6 | 5 | 6 | 4 | | 10 | 8 | 3 | 6 | 9 | 7 | |
| β-90 | 1.25 | 9 | 10 | 8 | 7 | | 10 | 9 | 6 | 7 | 10 | 6 | 21 |
|  | 0.31 | 8 | 9 | 7 | 5 | | 10 | 8 | 6 | 6 | 10 | 6 | |
| β-91 | 1.25 | 9 | 10 | 10 | | 9 | 10 | 9 | 9 | 10 | 10 | 9 | 21 |
|  | 0.31 | 9 | 9 | 9 | | 9 | 10 | 9 | 7 | 9 | 9 | 6 | |
| β-92 | 1.25 | 5 | 7 | 7 | | 9 | 10 | 10 | 6 | 5 | 6 | 3 | 20 |
| β-93 | 1.25 | 9 | 7 | 9 | | 10 | 10 | 9 | 7 | 9 | 10 | 7 | 22 |
|  | 0.31 | 9 | 6 | 8 | | 9 | 10 | 9 | 5 | 9 | 7 | 5 | |
| β-94 | 1.25 | 4 | 6 | 7 | 7 | | 9 | 7 | 6 | 9 | 9 | 3 | 21 |
|  | 0.31 | 3 | 3 | 4 | 6 | | 8 | 4 | 4 | 6 | 4 | 2 | |
| β-95 | 1.25 | 6 | 10 | 10 | 9 | | 10 | 9 | 6 | 6 | 6 | 5 | 20 |
|  | 0.31 | 5 | 9 | 9 | 8 | | 9 | 8 | 5 | 5 | 3 | 4 | |

Note:* The day of observation after foliar application.

TEST EXAMPLE 8

1/10000-are pot was filled with upland farming soil and sown with velvet leaf (*Abutilon theophrasti*). When the plant reached the 1.2-leaf stage, a predetermined amount of the herbicide of the present invention diluted with 5 l of water per are and admixed with 0.1 vol %, based on the aqueous solution, of an agricultural spreader ("Kusa Rino", produced by Nihon Nohyaku Co., Ltd.) was foliarly applied to the plant with a small spray gun. The herbicidal effect was visually observed 25 days after the foliar application and evaluated according to the rating system shown below. The results obtained are shown in Table 10.

Rating System:

| Rating | Percent Growth Inhibition (%) |
|---|---|
| 1 | 0–19 |
| 2 | 20–29 |
| 3 | 30–39 |
| 4 | 40–49 |
| 5 | 50–59 |
| 6 | 60–69 |
| 7 | 70–79 |
| 8 | 80–89 |
| 9 | 90–99 |
| 10 | 100 |

TABLE 10

| Active Ingredient | Amount of Active Ingredient (g/a) | Rating |
|---|---|---|
| Compound No. β-54 | 1.25 | 8 |
| " | 0.63 | 6 |
| " | 0.31 | 5 |
| " | 0.16 | 3 |
| Chlorimuron-ethyl | 0.08 | 9 |
| " | 0.04 | 8 |
| " | 0.02 | 6 |
| Fomesafen | 1.00 | 7 |
| " | 0.5 | 7 |
| " | 0.25 | 3 |
| Compound No. β-54 + Chlorimuron-ethyl | 1.25 + 0.08 | 10 |
| Compound No. β-54 + Chlorimuron-ethyl | 1.25 + 0.04 | 10 |
| Compound No. β-54 + Chlorimuron-ethyl | 1.25 + 0.02 | 10 |
| Compound No. β-54 + Chlorimuron-ethyl | 0.63 + 0.08 | 10 |
| Compound No. β-54 + Chlorimuron-ethyl | 0.63 + 0.04 | 10 |
| Compound No. β-54 + Chlorimuron-ethyl | 0.63 + 0.02 | 10 |
| Compound No. β-54 + Chlorimuron-ethyl | 0.31 + 0.08 | 10 |
| Compound No. β-54 + Chlorimuron-ethyl | 0.31 + 0.04 | 9 |
| Compound No. β-54 + Chlorimuron-ethyl | 0.31 + 0.02 | 9 |
| Compound No. β-54 + Chlorimuron-ethyl | 0.16 + 0.08 | 10 |
| Compound No. β-54 + Chlorimuron-ethyl | 0.16 + 0.04 | 9 |
| Compound No. β-54 + Chlorimuron-ethyl | 0.16 + 0.02 | 8 |
| Compound No. β-54 + Fomesafen | 1.25 + 1.00 | 10 |
| Compound No. β-54 + Fomesafen | 1.25 + 0.5 | 10 |
| Compound No. β-54 + Fomesafen | 1.25 + 0.25 | 10 |
| Compound No. β-54 + Fomesafen | 0.63 + 1.00 | 10 |
| Compound No. β-54 + Fomesafen | 0.63 + 0.5 | 10 |
| Compound No. β-54 + Fomesafen | 0.63 + 0.25 | 9 |
| Compound No. β-54 + Fomesafen | 0.31 + 1.00 | 10 |
| Compound No. β-54 + Fomesafen | 0.31 + 0.5 | 10 |
| Compound No. β-54 + Fomesafen | 0.31 + 0.25 | 8 |
| Compound No. β-54 + Fomesafen | 0.16 + 1.00 | 10 |
| Compound No. β-54 + Fomesafen | 0.16 + 0.5 | 9 |
| Compound No. β-54 + Fomesafen | 0.16 + 0.25 | 7 |

TEST EXAMPLE 9

1/10000-are pot was filled with upland farming soil and sown with velvet leaf. When the plant reached the 1-leaf stage, a predetermined amount of the herbicide of-the present invention diluted with 5 l of water per are and admixed with 0.1 vol %, based on the aqueous solution, of an agricultural spreader ("Kusa Rino") was foliarly applied to the plant with a small spray gun. On the 20th day from the application, the aerial part of the plant was weighed to obtain a percent growth inhibition according to Equation (1) (found value) and a Colby's value (calculated value) according to Equation (2) (see *Weed*, Vol. 15, pp. 20–22 (1967)). The results obtained are shown in Table 11 below.

$$\text{Percent Growth Inhibition (\%)} = \left(1 - \frac{\text{Fresh Weight of Aerial Part of Plant in Treated Plot}}{\text{Fresh Weight of Aerial Part of Plant in Untreated Plot}}\right) \times 100 \quad (1)$$

$$\text{Colby's Value } (E) = \alpha + \beta - \frac{\alpha \times \beta}{100} \quad (2)$$

Wherein α represents a percent growth inhibition when treated with an amount a (g/a) of herbicide A; β represents a percent growth inhibition when treated with amount b (g/a) of herbicide B; and E represents an expected percent growth inhibition when treated with a of herbicide A and b of herbicide B.

That is, if a percent growth inhibition (found value) is higher than a Colby's value (calculated value) by the above-mentioned calculation, it can be said that the activity brought by the combination of herbicides exhibits a synergistic action.

TABLE 11

| Active Ingredient | Amount of Active Ingredient (g/a) | Percent Growth Inhibition (%) Found | Percent Growth Inhibition (%) Calcd. |
|---|---|---|---|
| Compound No. β-54 | 0.63 | 86 | |
| " | 0.31 | 52 | |
| " | 0.16 | 19 | |
| Bentazon | 1.25 | 69 | |
| " | 0.63 | 17 | |
| Metribuzin | 0.16 | 89 | |
| Compound No. β-54 + Bentazon | 0.63 + 1.25 | 100 | 96 |
| Compound No. β-54 + Bentazon | 0.63 + 0.63 | 93 | 88 |
| Compound No. β-54 + Bentazon | 0.31 + 1.25 | 100 | 85 |
| Compound No. β-54 + Bentazon | 0.31 + 0.63 | 94 | 60 |
| Compound No. β-54 + Bentazon | 0.16 + 1.25 | 90 | 75 |
| Compound No. β-54 + Bentazon | 0.16 + 0.63 | 50 | 33 |
| Compound No. β-54 + Metribuzin | 0.63 + 0.16 | 100 | 98 |
| Compound No. β-54 + Metribuzin | 0.31 + 0.16 | 100 | 95 |
| Compound No. β-54 + Metribuzin | 0.16 + 0.16 | 100 | 91 |

TEST EXAMPLE 10

1/10000-are pot was filled with upland farming soil and sown with velvet leaf. When the plant reached the 1-leaf stage, a predetermined amount of the herbicide of the present invention diluted with 5 of water per are and admixed with 0.1 vol %, based on the aqueous solution, of an agricultural spreader ("Kusa Rino") was foliarly applied to the plant with a small spray gun. On the 20th day from the application, the aerial part of the plant was weighed to obtain a percent growth inhibition and a Colby's value in the same manner as in Test Example 9. The results obtained are shown in Table 12 below.

TABLE 12

| Active Ingredient | Amount of Active Ingredient (g/a) | Percent Growth Inhibition (%) Found | Percent Growth Inhibition (%) Calcd. |
| --- | --- | --- | --- |
| Compound No. β-54 | 0.63 | 66 | |
| " | 0.31 | 32 | |
| " | 0.16 | 12 | |
| Linuron | 0.25 | 61 | |
| " | 0.125 | 35 | |
| Compound No. β-54 + Linuron | 0.63 + 0.25 | 91 | 87 |
| Compound No. β-54 + Linuron | 0.63 + 0.125 | 84 | 78 |
| Compound No. β-54 + Linuron | 0.31 + 0.25 | 74 | 73 |
| Compound No. β-54 + Linuron | 0.31 + 0.125 | 69 | 56 |
| Compound No. β-54 + Linuron | 0.16 + 0.25 | 74 | 66 |
| Compound No. β-54 + Linuron | 0.16 + 0.125 | 55 | 43 |

TEST EXAMPLE 11

1/10000-are pot was filled with upland farming soil and sown with large crabgrass (*Digitaria adscendens*). When the plant reached the 2-leaf stage, a predetermined amount of the herbicide of the present invention diluted with 5 l of water per are and admixed with 0.1 vol %, based on the aqueous solution, of an agricultural spreader ("Kusa Rino") was foliarly applied to the plant with a small spray gun. On the 20th day from the application, the aerial part of the plant was weighed to obtain a percent growth inhibition and a Colby's value in the same manner as in Test Example 9. The results obtained are shown in Table 13 below.

TABLE 13

| Active Ingredient | Amount of Active Ingredient (g/a) | Percent Growth Inhibition (%) Found | Percent Growth Inhibition (%) Calcd. |
| --- | --- | --- | --- |
| Compound No. β-54 | 0.63 | 77 | |
| " | 0.31 | 24 | |
| " | 0.16 | 19 | |
| Linuron | 0.5 | 79 | |
| " | 0.25 | 68 | |
| " | 0.125 | 23 | |
| Compound No. β-54 + Linuron | 0.63 + 0.5 | 98 | 95 |
| Compound No. β-54 + Linuron | 0.63 + 0.25 | 98 | 93 |
| Compound No. β-54 + Linuron | 0.63 + 0.125 | 97 | 82 |
| Compound No. β-54 + Linuron | 0.31 + 0.5 | 96 | 84 |
| Compound No. β-54 + Linuron | 0.31 + 0.25 | 91 | 76 |
| Compound No. β-54 + Linuron | 0.31 + 0.125 | 87 | 41 |
| Compound No. β-54 + Linuron | 0.16 + 0.5 | 89 | 83 |
| Compound No. β-54 + Linuron | 0.16 + 0.25 | 78 | 74 |
| Compound No. β-54 + Linuron | 0.16 + 0.125 | 41 | 38 |

Formulation Examples of the herbicide of the present invention will now be described.

FORMULATION EXAMPLE 1

| | |
| --- | --- |
| (1) clay (trade name: Newlite) | 97 parts by weight |
| (2) a polyoxyethylene octyl-phenyl ether premixed with white carbon (trade name: Dikssol W-92) | 2 parts by weight |
| (3) Compound No. α-18 | 1 part by weight |

The above-mentioned components are mixed together and pulverized to form a dust.

FORMULATION EXAMPLE 2

| | |
| --- | --- |
| (1) Compound No. α-22 | 75 parts by weight |
| (2) a polycarboxylic acid type polymer (trade name: Demol EP powder) | 13.5 parts by weight |
| (3) NaCl | 10 parts by weight |
| (4) dextrin | 0.5 part by weight |
| (5) an alkyl sulfonate (trade name: TP-89121) | 1 part by weight |

The above-mentioned components are placed in a high-speed mixing granulator, admixed with 20 wt % of water, granulated, and dried to form water-dispersible granules.

FORMULATION EXAMPLE 3

| | |
| --- | --- |
| (1) kaolin | 78 parts by weight |
| (2) a condensate of sodium naphthalenesulfonate and formalin (trade name: Lavelin FAN) | 2 parts by weight |
| (3) a sodium polyoxyethylene alkylaryl ether sulfate premixed with white carbon (Trade name: Sorpol 5039) | 5 parts by weight |
| (4) white carbon (trade name: Carplex) | 15 parts by weight |

A mixture of the above-mentioned components (1) to (4) is mixed with Compound No. α-2 at a weight ratio of 9:1 to form a wettable powder.

FORMULATION EXAMPLE 4

| | |
| --- | --- |
| (1) diatomaceous earth | 63 parts by weight |
| (2) a polyoxyethylene alkyl-phenyl ether sulfate ammonium salt premixed with white carbon (trade name: Dikssol W-66) | 5 parts by weight |
| (3) a dialkyl sulfosuccinate premixed with white carbon (trade name: Dikssol W-09B) | 2 parts by weight |
| (4) Compound No. α-18 | 30 parts by weight |

The above-mentioned components are mixed together to form a wettable powder.

FORMULATION EXAMPLE 5

| | |
|---|---|
| (1) talc micropowder (trade name: Hi-Filler No. 10) | 33 parts by weight |
| (2) a dialkyl sulfosuccinate premixed with white carbon (trade name: Sorpol 5050) | 3 parts by weight |
| (3) a mixture of a polyoxyethylene alkylarylether sulfate and a polyoxyethylene monomethyl ether carbonate, premixed with white carbon (trade name: Sorpol 5073) | 4 parts by weight |
| (4) Compound No. α-22 | 60 parts by weight |

The above-mentioned components are mixed together to form a wettable powder.

FORMULATION EXAMPLE 6

| | |
|---|---|
| (1) Compound No. α-2 | 4 parts by weight |
| (2) corn oil | 79 parts by weight |
| (3) a mixture of a dialkyl sulfosuccinate polyoxyethylene nonylphenyl ether, polyoxyethylene hydrogenated castor oil and polyglycerol esters of fatty acid (trade name: Sorpol 3815) | 15 parts by weight |
| (4) a bentonite-alkylamino complex (trade name: New D Orben) | 2 parts by weight |

The above-mentioned components are uniformly mixed together and pulverized with a Dyno mill (manufactured by Willy A. Bachofen) to form a suspension concentrate.

FORMULATION EXAMPLE 7

| | |
|---|---|
| (1) clay (trade name: Newlite) | 97 parts by weight |
| (2) a polyoxyethylene octylphenyl ether premixed with white carbon (trade name: Dikssol W-92) | 2 parts by weight |
| (3) Compound No. β-5 | 1 part by weight |

The above-mentioned components are mixed together and pulverized to form a dust.

FORMULATION EXAMPLE 8

| | |
|---|---|
| (1) Compound No. β-1 | 75 parts by weight |
| (2) a polycarboxylic acid type polymer (trade name: Demol EP powder) | 13.5 parts by weight |
| (3) NaCl | 10 parts by weight |
| (4) dextrin | 0.5 part by weight |
| (5) an alkyl sulfonate (trade name: TP-89121) | 1 part by weight |

The above-mentioned components are placed in a high-speed mixing granulator, admixed with 20 wt % of water, granulated, and dried to form water-dispersible granules.

FORMULATION EXAMPLE 9

| | |
|---|---|
| (1) kaolin | 78 parts by weight |
| (2) a condensate of sodium naphthalenesulfonate and formalin (trade name: Lavelin FAN) | 2 parts by weight |
| (3) a sodium polyoxyethylene alkylaryl ether sulfate premixed with white carbon (Trade name: Sorpol 5039) | 5 parts by weight |
| (4) white carbon (trade name: Carplex) | 15 parts by weight |

A mixture of the above-mentioned components (1) to (4) is mixed with Compound No. β-54 at a weight ratio of 9:1 to form a wettable powder.

FORMULATION EXAMPLE 10

| | |
|---|---|
| (1) diatomaceous earth | 63 parts by weight |
| (2) a polyoxyethylene alkylphenyl ether sulfate ammonium salt premixed with white carbon (trade name: Dikssol W-66) | 5 parts by weight |
| (3) a dialkyl sulfosuccinate premixed with white carbon (trade name: Dikssol W-09B) | 2 parts by weight |
| (4) Compound No. β-2 | 30 parts by weight |

The above-mentioned components are mixed together to form a wettable powder.

FORMULATION EXAMPLE 11

| | |
|---|---|
| (1) talc micropowder (trade name: Hi-Filler No. 10) | 33 parts by weight |
| (2) a dialkyl sulfosuccinate premixed with white carbon (trade name: Sorpol 5050) | 3 parts by weight |
| (3) a mixture of a polyoxyethylene alkylarylether sulfate and a polyoxyethylene monomethyl ether carbonate, premixed with white carbon (trade name: Sorpol 5073) | 4 parts by weight |
| (4) Compound No. β-3 | 60 parts by weight |

The above-mentioned components are mixed together to form a wettable powder.

FORMULATION EXAMPLE 12

| | |
|---|---|
| (1) Compound No. β-4 | 4 parts by weight |
| (2) corn oil | 79 parts by weight |
| (3) a mixture of a dialkyl sulfosuccinate, polyoxyethylene nonylphenyl ether, polyoxyethylene hydrogenated castor oil and polyglycerol esters of fatty acid (trade name: Sorpol 3815) | 15 parts by weight |
| (4) a bentonite-alkylamino complex (trade name: | 2 parts by weight |

-continued

New D Orben)

The above-mentioned components are uniformly mixed together and pulverized with a Dyno mill (manufactured by Willy A. Bachofen) to form a suspension concentrate.

While the invention has been described in detail and with reference to specific embodiments thereof, it will be apparent to one skilled in the art that various changes and modifications can be made therein without departing from the spirit and scope thereof.

What is claimed is:

1. A pyridinesulfonamide compound or its salt represented by the following formula (I):

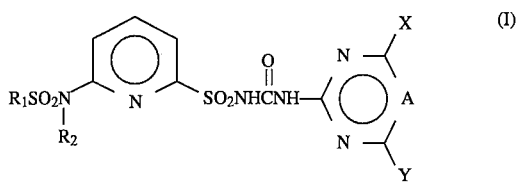

wherein A is CH; $R_1$ and $R_2$ are each independently a member selected from the group consisting of $C_{1-6}$ alkyl groups which are optionally substituted with one or more substituents selected from the group consisting of halogen atoms and $C_{1-6}$ alkoxy groups, $C_{2-6}$ alkenyl groups which are optionally substituted with one or more substituents selected from the group consisting of halogen atoms and $C_{1-6}$ alkoxy groups, $C_{3-6}$ cycloalkyl groups which are optionally substituted with one or more substituents selected from the group consisting of halogen atoms, $C_{1-6}$ alkyl groups and $C_{1-6}$ alkoxy groups, and phenyl groups which are optionally substituted with one or more substituents selected from the group consisting of halogen atoms, $C_{1-6}$ alkyl groups, $C_{1-6}$ haloalkyl groups, and nitro groups; and X and Y are each independently a member selected from the group consisting of $C_{1-6}$ alkyl groups and $C_{1-6}$ alkoxy groups.

2. The compound or the salt thereof as in claim 1, wherein $R_1$ and R2 are each independently a member selected from the group consisting of $C_{1-6}$ alkyl groups which are optionally substituted with one or more substituents selected from the group consisting of halogen atoms and $C_{1-6}$ alkoxy groups and $C_{3-6}$ cycloalkyl groups which are optionally substituted with one or more substituents selected from the group consisting of halogen atoms, $C_{1-6}$ alkyl groups and $C_{1-6}$ alkoxy groups.

3. The compound or the salt thereof as in claim 1, wherein $R_1$ and $R_2$ are each independently a member selected from the group consisting of $C_{1-6}$ alkyl groups, $C_{1-6}$ haloalkyl groups, and $C_{3-6}$ cycloalkyl groups.

4. The compound or the salt thereof as in claim 1, which is 6-[(N-ethyl-N-methylsulfonyl)amino]-N-[[(4,6-dimethoxypyrimidin-2-yl)amino]carbonyl]- 2-pyridinesulfonamide.

5. The compound or the salt thereof as in claim 1, which is 6-[(N-ethyl-N-ethylsulfonyl)amino]-N-[[(4,6-dimethoxypyrimidin-2-yl)amino]carbonyl]- 2pyridinesulfonamide.

6. The compound or the salt thereof as in claim 1, which is 6-[(N-ethyl-N-isopropylsulfonyl)amino]-N-[[(4,6-dimethoxypyrimidin-2-yl)amino]carbonyl]- 2-pyridinesulfonamide.

7. A herbicidal composition containing as the effective ingredient a pyridinesulfonamide compound or its salt represented by the following formula (I), and an inert carrier:

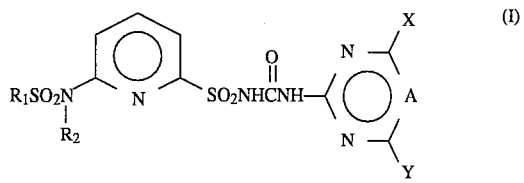

wherein A is CH; $R_1$ and $R_2$ are each independently a member selected from the group consisting of $C_{1-6}$ alkyl groups which are optionally substituted with one or more substituents selected from the group consisting of halogen atoms and $C_{1-6}$ alkoxy groups, $C_{2-6}$ alkenyl groups which are optionally substituted with one or more substituents selected from the group consisting of halogen atoms and $C_{1-6}$ alkoxy groups, $C_{3-6}$ cycloalkyl groups which are optionally substituted with one or more substituents selected from the group consisting of halogen atoms, $C_{1-6}$ alkyl groups and $C_{1-6}$ alkoxy groups, and phenyl groups which are optionally substituted with one or more substituents selected from the group consisting of halogen atoms, $C_{1-6}$ alkyl groups, $C_{1-6}$ haloalkyl groups, and nitro groups; and X and Y are each independently a member selected from the group consisting of $C_{1-6}$ alkyl groups and $C_{1-6}$ alkoxy groups.

8. The herbicidal composition as in claim 7, wherein $R_1$ and $R_2$ are each independently a member selected from the group consisting of $C_{1-6}$ alkyl groups which are optionally substituted with one or more substituents selected from the group consisting of halogen atoms and $C_{1-6}$ alkoxy groups, and $C_{1-6}$ cycloalkyl groups which are optionally substituted with one or more substituents selected from the group consisting of halogen atoms, $C_{1-6}$ alkyl groups and $C_{1-6}$ alkoxy groups.

9. The herbicidal composition as in claim 7, wherein $R_1$ and $R_2$ are each independently a member selected from the group consisting of $C_{1-6}$ alkyl groups, $C_{1-6}$ haloalkyl groups, and $C_{3-6}$ cycloalkyl groups.

10. The herbicidal composition as in claim 7, wherein said effective ingredient is 6-[(N-ethyl-N-methylsulfonyl)amino]-N-[[(4,6-dimethoxypyrimidin-2-yl)-amino]carbonyl]-2-pyridinesulfonamide.

11. The herbicidal composition as in claim 7, wherein said effective ingredient is 6-[(N-ethyl-N-ethylsulfonyl)amino]-N-[[(4,6-dimethoxypyrimidin-2-yl)-amino]carbonyl]- 2-pyridinesulfonamide.

12. The herbicidal as in claim 7, wherein said effective ingredient is 6-[(N-ethyl-N-isopropylsulfonyl)amino]-N-[ [(4,6-dimethoxypyrimidin-2-yl)amino] carbonyl]-2-pyridinesulfonamide.

13. A herbicidal method which comprises applying to plants a herbicidally effective amount of a pyridinesulfonamide compound or its salt represented by the following formula (I):

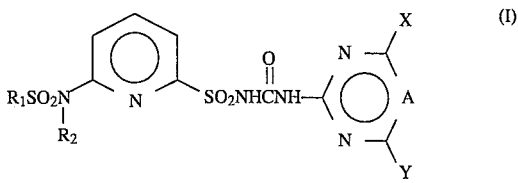

wherein A is CH; $R_1$ and $R_2$ are each independently a member selected from the group consisting of $C_{1-6}$ alkyl groups which are optionally substituted with one or more substituents selected from the group consisting of halogen atoms and $C_{1-6}$ alkoxy groups, $C_{2-6}$ alkenyl groups which are optionally substituted with one or more substituents selected from the group consisting of halogen atoms and $C_{1-6}$ alkoxy groups, $C_{3-6}$ cycloalkyl groups which are optionally substituted with one or more substituents selected from the group consisting of halogen atoms, $C_{1-6}$ alkyl groups and $C_{1-6}$ alkoxy groups, and phenyl groups which are optionally substituted with one or more substituents selected from the group consisting of halogen atoms, $C_{1-6}$ alkyl groups, $C_{1-6}$ haloalky groups, and nitro groups; and X and Y are each independently a member selected from the group consisting of $C_{1-6}$ alkyl groups and $C_{1-6}$ alkoxy groups.

* * * * *